US011191977B1

(12) United States Patent
Letovsky

(10) Patent No.: US 11,191,977 B1
(45) Date of Patent: Dec. 7, 2021

(54) APPLICATIONS OF BIOACTIVE FREQUENCIES AND MENUS THEREOF

(71) Applicant: Howard Letovsky, Willits, CA (US)

(72) Inventor: Howard Letovsky, Willits, CA (US)

( * ) Notice: Subject to any disclaimer, the term of this patent is extended or adjusted under 35 U.S.C. 154(b) by 0 days.

(21) Appl. No.: 17/096,823

(22) Filed: Nov. 12, 2020

(51) Int. Cl.
*A61H 23/00* (2006.01)
*A61N 7/00* (2006.01)
*A61N 5/06* (2006.01)
*A61H 23/02* (2006.01)
*G16H 20/40* (2018.01)

(52) U.S. Cl.
CPC ....... *A61N 5/0613* (2013.01); *A61H 23/0236* (2013.01); *G16H 20/40* (2018.01); *A61H 2201/10* (2013.01); *A61H 2230/105* (2013.01); *A61N 2005/0659* (2013.01); *A61N 2005/0661* (2013.01); *A61N 2005/0663* (2013.01); *A61N 2007/0004* (2013.01)

(58) Field of Classification Search
CPC .......... A61N 5/0613; A61N 2005/0661; A61N 2005/0659; A61N 2005/0663; A61N 2007/0004; A61H 23/0236; A61H 2201/10; A61H 2230/105; G16H 20/40
See application file for complete search history.

(56) References Cited

U.S. PATENT DOCUMENTS

| | | |
|---|---|---|
| 4,561,961 A | 12/1985 | Hofmann |
| 5,304,486 A | 4/1994 | Chang |
| 5,472,441 A | 12/1995 | Edwards |
| 5,922,209 A | 7/1999 | Koshida |
| 6,400,487 B1 | 6/2002 | Harris |
| 6,790,341 B1 | 9/2004 | Saban |
| 8,278,629 B2 | 10/2012 | Chang |
| 8,927,264 B2 | 1/2015 | Letovsky |
| 2003/0032900 A1* | 2/2003 | Ella .................. A61H 7/008 601/6 |
| 2011/0040295 A1* | 2/2011 | Pierce .............. A61L 2/0011 606/11 |
| 2011/0178441 A1* | 7/2011 | Tyler ............... A61N 5/062 601/2 |
| 2015/0005569 A1* | 1/2015 | Missoli ............ A61N 2/02 600/9 |

FOREIGN PATENT DOCUMENTS

WO WO-2020223242 A1 * 11/2020 ............. A61B 18/00

* cited by examiner

*Primary Examiner* — Quang D Thanh
(74) *Attorney, Agent, or Firm* — Eric Kelly

(57) ABSTRACT

A treatment tool may generate and transmit a predetermined bioactive frequency and/or waveform of electromagnetic energy and/or acoustic energy into a given region of treatment for inducing a particular cellular outcome/behavior of at least one targeted cell selected from the region of treatment. The region of treatment may be at least a single organism or portion thereof. The region of treatment may include other different types of cells in addition to the at least one targeted cell. The treatment tool may be used in vivo, non-invasively, and selectively, wherein the particular cellular outcome/behavior occurs in the at least one targeted cell but not other cells. The treatment tool may have a transmitter assembly, an antenna tuner, an attenuator, a broadband power amplifier, and a frequency/waveform generator; and the treatment tool may also have a computer. The treatment tool may be used to treat cancers and/or other conditions.

44 Claims, 14 Drawing Sheets

| Cell Type | Bioactive Frequencies Characteristics | Effect(s) on Cell Type |
|---|---|---|
| Human Prostate Cancer<br><br>(LCVMSProstate Cancer Frequency Set 1)* | 450 hertz (Hz) square, 2008 Hz square, 4000 Hz ramp, 6022 Hz square, 14000 Hz sine, 20000 Hz sine; with durations from two to eight minutes | Destructive effects include cessation of mitosis, apoptosis, necrosis, increased cell membrane permeability, protein misfolding, and granulation of cellular mechanics. |
| Human Prostate Cancer<br><br>(LCVMS Prostate Cancer Frequency Set 2)* | 450 Hz, 489 Hz, 583 Hz, 971.3 Hz, 4000 Hz, 6022 Hz, 7402 Hz, 10542 Hz, 11300 Hz; all square waveforms; with durations of eight minutes | Destructive effects include cessation of mitosis, apoptosis, necrosis, increased cell membrane permeability, protein misfolding, and granulation of cellular mechanics. |
| Human Prostate Cancer<br><br>(LCVMS Cancer Frequency Set 3 [most derived from tracking generator absorption analysis])* | 317 kilohertz (kHz), 544 kHz, 947 kHz, 1.220 megahertz (MHz), 2.467 MHz, 4.812 MHz, 5.265455 MHz, 5.9 MHz, 11.300 MHz, 11.780 MHz, 17.045455 MHz, 28.823455 MHz; sine waves; 30 minutes (min.) each | Destructive effects include cessation of mitosis, apoptosis, necrosis, increased cell membrane permeability, protein misfolding, and granulation of cellular mechanics. |
| Human Prostate Cancer<br><br>(LCVMS Cancer Frequency Sets 4 [all tracking generator absorption analysis])* | 157.8 MHz, 1.1495 gigahertz (GHz), 1.153 GHz, 1.356 GHz,1.393 GHz, 1.4108 – 1.4760 GHz, 1.579 GHz, 1.612 – 1.617 GHz, 1.660 GHz, 1.889 GHz, 1.975 GHz, 2.455 GHz; sine and square waveforms | Destructive effects include cessation of mitosis, apoptosis, necrosis, increased cell membrane permeability, protein misfolding, and granulation of cellular mechanics. |
| Human Prostate Cancer<br><br>(Pulsed signals that showed significant electrical behavior changes) | 278.44 kHz; 6.440 kHz (initiated regular spiking that stayed after signal was shut off); 840 kHz (initiated regular spiking that stayed after signal was shut off); 1.328 MHz; 1.330.440 MHz; 1.365.440 MHZ; 1.348 MHZ;All the above with waveform width of 107 milliseconds and duty cycle of 16% (duty cycle of generator) | Destructive effects include cessation of mitosis, apoptosis, necrosis, increased cell membrane permeability, protein misfolding, and granulation of cellular mechanics. |

FIG. 12A (Table 1 [part 1 of 2])

| | | |
|---|---|---|
| Human Prostate Cancer<br><br>(Pulsed signals that showed significant electrical behavior changes) | 278.44 kHz; 6.440 kHz (initiated regular spiking that stayed after signal was shut off); 840 kHz (initiated regular spiking that stayed after signal was shut off); 1.328 MHz; 1.330 MHz; 1.365 MHZ; 1.348 MHZ;All the above with waveform width of 107 milliseconds and duty cycle of 16% (duty cycle of generator) | Destructive effects include cessation of mitosis, apoptosis, necrosis, increased cell membrane permeability, protein misfolding, and granulation of cellular mechanics. |
| Human Prostate Cancer | 1960 Hz square; 1980 Hz square; 2029 Hz square; 2036 Hz ramp; 2040 Hz ramp; 2417 Hz square; 2020 Hz ramp; 2060 Hz ramp; 2127 Hz ramp; 2634 Hz ramp; 3826 Hz ramp; 7426 Hz; 1170 Hz sine/ramp; 1400 Hz ramp; 1680 Hz ramp; 6982 Hz pulse at 30.2 milliseconds and 21%duty cycle (duty cycle of generator); 11612 Hz square waveform | Destructive effects include cessation of mitosis, apoptosis, necrosis, increased cell membrane permeability, protein misfolding, and granulation of cellular mechanics. |
| Human Prostate Cancer<br><br>(Boris Pasche breast, prostate, and pancreatic Common Frequencies) | 1,873.477 Hz, 2,221.323 Hz, 6,350.333 Hz, and 10,456.383 Hz; duration of 15 minutes | No significant effects observed after exposure. (Frequencies alleged to have effects on breast, prostate and pancreatic cancers by Boris Pasche.) |
| Human Prostate Cancer<br><br>(Yoram Palti Novocure Frequencies) | 150MHz and 200MHz | No significant effects observed after exposure. (Frequencies alleged to have effects on cancer by Yoram Palti Novocure.) |
| Human Lymphoma Cancer | 971 Hz (square or sine), 9309 Hz (square or sine), 10609Hz (square or sine) for one hour per day over at three consecutive days up to fifteen days;using 2.4 MHz or 3.5 MHz carrier wave; in-vivo | Total/complete human lymphoma cancer cell destruction within 24 hours of exposure |

FIG. 12B (Table 1 [part 2 of 2])

APPLICATIONS OF BIOACTIVE FREQUENCIES AND MENUS THEREOF

CROSS REFERENCE TO RELATED PATENTS

This present U.S. non-provisional patent application is related to a previous U.S. Pat. No. 8,927,264, by the same inventor; wherein the disclosure and the content of which is incorporated herein by reference in its entirety as if fully set forth below.

TECHNICAL FIELD OF THE INVENTION

The present invention relates to using a mildly invasive sensor tool to determine how living cells, in vivo, respond to electromagnetic energy of predetermined and particular characteristics; and to using electromagnetic energy of predetermined and particular characteristics to induce desired outcomes in living cells, also in an in vivo setting, such as, but not limited, to treatments using the outputted electromagnetic energy of predetermined and particular characteristics.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Much of modern western medicine concerns itself within using various drugs (whether synthesized or bio-produced) to treat various undesired conditions (e.g., arthritis) and/or more often to reduce effects stemming from the given undesired condition (e.g., pain). Depending upon the given undesired condition and/or the effects stemming from the given undesired condition, such drugs may be perfectly adequate (e.g., antibiotics for a non-resistive bacterial infection); whereas, for other undesired conditions there may be no known adequate drug, or the known drugs have undesired side effects, or the harm from the known drug may outweigh its efficacy. Drug based therapies also have run into problems of tolerance, resistance, and/or addiction.

Drug based therapeutic uses often run into problems when there is a need to specifically target only one type of cell/tissue and/or a specific location needing treatment that may be largely inaccessible, being located within a human body. For example, consider cancer. Many cancers begin in a given tissue type, often entirely within the given host animal making both diagnosis and treatment historically difficult. Drugs used to fight cancer, via chemotherapy, suffer the problem of harming both normal/healthy/natural cells and cancer cells. Chemotherapy drugs cannot differentiate between normal cells and cancer cells and thus harm both cell types. That is, chemotherapy drugs are indiscriminate with respect to the type of cell being harmed by the chemotherapy drugs. Similarly, ionizing radiation as a cancer treatment tool is of such high energy that it cannot differentiate between normal cells and cancer cells and thus harms both cell types. There is a need of another treatment modality that can specifically and reliably target cancer cells without targeting non-cancer cells. And taking this concept a step further, there is a need of a treatment modality that can specifically target cells/tissue of a predetermined/particular cell type, but without targeting cells/tissue of a different predetermined/particular cell type.

The present invention and its embodiments largely concerns itself with using "bioactive" electromagnetic energy of predetermined and particular characteristics to induce desired outcomes/behaviors in living cells of a particular cell type, but without inducing the same outcomes in living cells of a different particular type, and in an in vivo setting. The electromagnetic energy of predetermined and particular characteristics (e.g., bioactive frequencies and/or bioactive waveforms) that may induce desired outcomes/behaviors in living cells of a particular cell type, but without inducing the same outcomes in living cells of a different particular type may be determined by the present inventor's tool set inventions and its embodiments disclosed and taught in his prior U.S. Pat. No. 8,927,264; and/or from a new mildly invasive sensor tool taught herein.

However, the cellular outcomes induced by the bioactive electromagnetic energy of predetermined and particular characteristics that the present invention and its embodiments concerns itself with are not the previously known uses of high/strong electromagnetic energy for indiscriminate cellular death and/or indiscriminate cellular cooking, as in UV sterilization, cancer radiation therapy, and/or microwave cooking, that kills and/or cooks all exposed cells regardless of cell type. Rather, the bioactive electromagnetic energy of predetermined and particular characteristics taught herein are for inducing particular cellular outcomes/behaviors that may be specific to one type of cell/tissue while having no to negligible outcome on cells/tissue of different types, resulting in a substantially non-invasive, yet highly discriminate/targeted, therapeutic tool capable of targeting specific cell/tissue types for particular outcomes without inducing those particular outcomes in cells/tissues of other types.

The determination of the electromagnetic energy of predetermined and particular characteristics that are of concern herein (i.e., the bioactive frequencies), from the present inventor's tool set inventions and its embodiments disclosed and taught in his prior U.S. Pat. No. 8,927,264, have led to therapeutic applications disclosed herein, including devices, apparatus, and/or systems for administering those therapeutic applications in in vivo settings. A short recap on the history leading up to U.S. Pat. No. 8,927,264 and of some prior art is in order.

The effects of electromagnetic fields on living tissue likely dates back to the first discoveries that lighting strikes can be detrimental to living things—which is another example of high/strong electromagnetic energy being used destructively in an indiscriminate matter, regardless of cell/tissue type, wherein the exposed living tissue essentially cooks as the current is sufficiently high to heat the living tissue to lethal cellular levels before that heat energy can be dissipated. In our modern era, the study of the effects of electromagnetic fields on living tissue has a history dating back to likely the 1920s.

In the 1920s and the 1930s, Royal Raymond Rife researched the effects of audio and low RF (radio) frequencies on many organisms such as bacteria, viruses, and human cells, including some cancer cells. He claimed to have found frequencies that would allegedly cure cancer through the elimination of viruses that had invaded the cells. (As we've now learned today (circa 2020), most cancers have nothing to do with a virus; although a limited number of cancers may be caused by particular virus.) Rife's efforts and results were universally discredited by the FDA and AMA—though products derived from his research, and frequency sets which he developed are still used all over the world to allegedly resolve a myriad of ailments—including cancer.

Next, are some examples of electromagnetic tools being used in a variety of therapeutic arenas. Dr. Tarak El-Bialy of the Faculty of Medicine and Dentistry at the University of Alberta has successfully regenerated teeth from the root up by the application of specifically configured 1.5 megahertz (MHz) pulses. Also, electrical stimulation for bone growth is now common throughout the world using specifically configured frequencies at 76.4 hertz (Hz) in the Donjoy Global CMF line of products. Further, therapeutic "cold" lasers (1024 nm) such as those offered by Donjoy Global in their Vectra Genisys product line have been shown to: increase cell metabolism; increase collagen synthesis for increased healing of soft tissues; increase in circulation through increased formation of new capillaries by release of growth factors; increase T-cell production for increased immune function; increase production of neurotransmitters such as endorphins, serotonin, and ACTH; and increase chronic pain threshold through decreased C-fiber activity.

Next, some prior patents that may relate to some embodiments of the present invention are presented herein with summaries of their abstracts. The Yoshida et al. U.S. Pat. No. 5,922,209, describes a process for deactivating or destroying microorganisms by applying electrical energy to a microorganism through a liquid, gas, or solid having electrical energy to cause an increase in an electric charge in excess of the limit of intracellular and extracellular electrostatic capacity possessed by the microorganism, which in turn results in an irreversible change in the microorganism cells and/or explosively destroys the border membrane of the microorganism cells.

Chang's U.S. Pat. No. 5,304,486, discloses a method of and apparatus for cell poration and cell fusion using radiofrequency electrical pulses. The method can be used to fuse or porate a variety of cells including animal cells, human cells, plant cells, protoplasts, erythrocyte ghosts, liposomes, vesicles, bacteria, and yeasts. The method can also be used to produce new biological species, to make hybridoma cells which produce animal or human monoclonal antibodies and to insert therapeutic genes into human cells which can be transplanted back into the human body to cure genetic diseases.

The Saban, et al. U.S. Pat. No. 6,790,341, provides microband electrode array sensors for detecting the presence and measuring the concentration of analytes in a sample. The microband electrodes of U.S. Pat. No. 6,790,341, have both a width and thickness of microscopic dimensions. Preferably the width and thickness of the microband electrodes are less than the diffusion length of the analyte(s) of interest. The electrodes are separated by a gap insulating material that is large enough that the diffusion layers of the electrodes do not overlap such that there is no interference and the currents at the electrodes are additive.

Edwards, et al. U.S. Pat. No. 5,472,441, discloses a device for treating body tissues containing cancerous cells or non-malignant tumors with RF ablation, alone or in combination with systemic or localized chemotherapy.

The Harris, et al. U.S. Pat. No. 6,400,487, teaches methods and apparatus for screening large numbers of chemical compounds and performing a wide variety of fluorescent assays, including live cell assays. The methods utilize a laser line scan confocal microscope with high speed, high resolution and multi-wavelength capabilities and real time data-processing.

Chang's U.S. Pat. No. 8,278,629, discloses live-cell observation equipment for a non-light-transmitting microscope to study temperature-dependent events and method thereof.

Hofmann's U.S. Pat. No. 4,561,961, describes a cooled microscope slide and electrode apparatus for use in live cell fusion system employing tubular electrodes so fluid may be pumped through the electrodes to dissipate heat to enhance the yield of viable hybrids. An alternate embodiment sandwiches a gasket and parallel tubular electrodes between glass slides to permit cell fusion in a closed sterile environment.

And as previously noted, the present inventor's own U.S. Pat. No. 8,927,264, by the same inventor of this present patent application, disclosed and taught a tool set for determining the bioactive electromagnetic energy of in-vitro predetermined and particular characteristics that may result in and/or induce particular cellular outcomes/behaviors. Prior to the U.S. Pat. No. 8,927,264, the art was missing a means for the logical and the systematic determination of these bioactive electromagnetic energy of predetermined and particular characteristics that may result in and/or induce particular cellular outcomes/behaviors for a particular cell/tissue type. Prior to the U.S. Pat. No. 8,927,264, any known bioactive electromagnetic energy of predetermined and particular characteristics that may result in and/or induce particular cellular outcomes/behaviors for a particular cell/tissue type was essentially the result of luck and guesswork. Prior to the U.S. Pat. No. 8,927,264, there were glaring gaps in the known bioactive frequencies and their associated cellular effects.

However, now that tool sets as taught by the U.S. Pat. No. 8,927,264 are in use, a comprehensive determination of all the bioactive electromagnetic energy of predetermined and particular characteristics that may result in and/or induce particular cellular outcomes/behaviors for a particular cell/tissue type is in progress; and the present invention largely concerns itself with using those determined bioactive frequencies for therapeutic applications using the devices, apparatus, and/or systems taught herein.

Also note, using tool sets other than those taught by the U.S. Pat. No. 8,927,264, alleged bioactive frequencies as published by others (e.g., Boris Pasche and Yoram Palti Novocure Frequencies) have been tested and found to be largely non-bioactive with respect to human prostate cancer cells—but may have shown effectiveness in the cessation of mitosis in other cancers (Novocure).

A natural question related to these technologies, may be why do cells/tissue of a particular type respond in predictable (consistent) ways to electromagnetic energy of predetermined and particular characteristics, when other different types of cells/tissue may not so respond to that very same electromagnetic energy of predetermined and particular characteristics. The reason stems from what differentiates one cell type from another—which is largely the given cell types specific molecular makeup. For example, a bacterial cell is easily differentiated from eukaryotic cells; a fungal cell is easily distinguished from a plant/algae cell and/or from an animal cell; a skin cell is easily differentiated from a red blood cell; a muscle cell is easily differentiated from a gland; a cancer cell is easily differentiated from a non-cancer cell; etc. While such differentiating may be done through genetic analysis; phenotypic and/or visual analysis is often all that is necessary to make these differentiations—based largely on microscopically visible differences in molecular/cellular structures; such as, but not limited to, differences in the cell membranes, cell walls (for species with cell walls), and/or molecules (e.g., hormones or neurotransmitters) that are outputted from a given cell type and/or molecules that are taken into or from a given cell type. And these differences in things like cell membranes, cell walls, molecule output/input in turn stem in large part from differences in proteins, lipids, glycoproteins, structural carbohydrates, and/or the like of the given cell type. That is, what differentiates one cell type from another is its particular makeup of molecules (e.g., especially proteins, but also, lipids, fatty acids, and carbohydrates), including in terms of different molecule types, molecule distribution in the given cell, molecule quantity in the given cell, cellular structures resulting from those molecules (e.g., cell membranes, cell walls, protein channels, etc.), etc. For example, a nerve cell (e.g., with its myelin sheath) will have different cellular structures (as a result of its different specific molecular makeup) as compared to a pancreas cell (e.g., that is programmed to output various hormones). And different molecules will respond differently from exposure to the same electromagnetic energy of a same and predetermined characteristic. Thus, different cell types will respond differently from exposure to the same electromagnetic energy of a same and predetermined characteristic because of the molecular differences characteristic of each particular cell type. Each different cell type has its own unique electromagnetic profile/fingerprint (e.g., which may be visualized by an EEG a given cell type).

Turning to an example of cancer in humans. The human body is made up of cells. Groups of similar cell types form specific tissues. Each of the cells of the human body is spatially defined from other cells in the human body by the given cell's outer cell membrane. This outer cell membrane is made from phospholipids. Phospholipids are characterized by a highly polar and charged headgroup and a non-polar (non-charged) lipid tail. The polar headgroups oppose and repel each other and form hydrogen bonds with water. The non-polar side chains (tails) are attracted to each other and stick to each other through van der waals forces. The net effect of these interactions results in a lipid bilayer (with cytoplasm on the inside) which is largely impermeable except to small molecules and some lipids. The lipid bilayer of each cell is the "matrix" in which the body performs many of its functions. The lipid bilayer is also the physical barrier used to create subcellular compartments in which specialized biological functions can occur in isolation from other parts of the cell (e.g., sub-cell organelles, such as, but not limited to the nucleus). Due to the largely impermeability of the lipid bilayer to charged molecules, the transport of materials and charged molecules need to be ferried through the cell membrane using specialized proteins. Specialized proteins embedded in the cellular membrane perform this function, i.e., various protein channels in the lipid bilayer. Due to the impermeability of the cell membrane to charged molecules, the membrane itself can become polarized. Both the polarization and the lipid composition of the membrane affect the biological activity of the proteins embedded in the membrane. Because the different cell types of the human body have different membrane compositions (such as, but not limited to cell membrane proteins and/or lipids) and different internal molecular compositions, each cell type has a unique electromagnetic resonance frequency profile/fingerprint and tolerance windows—because different molecules respond differently to the same electromagnetic energy. When cell types become cancerous or damaged, the membrane structure is significantly altered. Electromagnetically, the cancer cell becomes a different cell type with its own unique electromagnetic profile. That is, a normal pancreas cell is electromagnetically different from a cancerous pancreas cell—they each have a different electromagnetic resonance frequency profile/fingerprint and tolerance windows. Externally applied electromagnetic radiation can synchronize to and modulate any pre-existing resonating system, including cells and/or tissue. This synchronization and modulation can be used to stimulate, suppress, damage, or even burst the lipid bilayer of a given cell type, without doing so in a different cell type. By targeting specific cell types, using electromagnetic radiation of specific and predetermined characteristics, one can alter the function of the membrane-bound proteins and/or of the membrane lipids in that cell type in a very precise and reproducible way. This alteration can be used to either restore or block the function of specific proteins, with the same or even better specificity as traditional small molecule agonists and antagonists (e.g., drugs), and often without significant side effects.

In sum, there is a need in the art for devices, apparatus, and/or systems that can output electromagnetic energy (and/or acoustic energy) of a specific and particular characteristic to achieve and/or induce a particular cellular outcome/behavior in cell(s) of a particular cell type, without inducing that particular cellular outcome/behavior in a different particular cell type(s).

It is to these ends that the present invention has been developed.

BRIEF SUMMARY OF THE INVENTION

To minimize the limitations in the prior art, and to minimize other limitations that will be apparent upon reading and understanding the present specification, some embodiments of the present invention may describe an electro medical tool, a sensor tool, a treatment tool, systems thereof, and/or methods of using such tool(s).

The electro medical tool and/or the sensor tool may be used for determining frequencies and/or waveforms of electromagnetic energy and/or acoustic energy that may be bioactive, resulting in and/or inducing a particular and reproducible cellular outcome/behavior in a particular type of cell; and in some embodiments, without resulting in and/or inducing that particular cellular outcome/behavior in a different particular type of cell. The electro medical tool may be used in in vitro settings (or in in vivo setting when the cell(s) being tested are a single celled organism). The sensor tool may be mildly invasive and used in an in vivo setting, wherein the cells tested still reside within the given organism/patient being worked on.

The treatment tool may generate and transmit a predetermined bioactive frequency and/or waveform of electromagnetic energy and/or acoustic energy into a given region of treatment for inducing a particular cellular outcome/behavior of at least one targeted cell selected from the region of treatment. The predetermined bioactive frequency and/or waveform of electromagnetic energy and/or acoustic energy that induces the particular cellular outcome/behavior of at least one targeted cell may be determined by use of the electro medical tool set (e.g., U.S. Pat. No. 8,927,264 and/or as taught herein) and/or by use of the sensor tool. The region of treatment may be at least a single organism or portion thereof. The region of treatment may include other different types of cells in addition to the at least one targeted cell. The treatment tool may be used in vivo, non-invasively, and selectively, wherein the particular cellular outcome/behavior occurs in the at least one targeted cell but not in other different cell types of the region of treatment. The treatment tool may have a transmitter assembly, an impedance matching network (including an antenna tuner and an attenuator), a broadband power amplifier, and a frequency/waveform generator; and the treatment tool may also have a computer.

The treatment tool may be used to treat undesired cell(s) or to treat desired cell(s). The treatment tool may be used to treat cancers and/or other conditions. Through exposure of the predetermined bioactive frequency and/or waveform of electromagnetic energy and/or acoustic energy that induces the particular cellular outcome/behavior, the undesired cell(s) may be: induced to die; caused to have increase cell membrane permeability for selective uptake of chemotherapy drug(s); caused to have increase cell membrane permeability for selective uptake of markers that make the tagged undesirable cell more visible by the host's immune system for immune system attack and destruction; cessation of mitosis (and/or meiosis); enter a state of apoptosis; enter a state of necrosis; portions thereof; combinations thereof; and/or the like. Through exposure of the predetermined bioactive frequency and/or waveform of electromagnetic energy and/or acoustic energy that induces the particular cellular outcome/behavior, the undesired cell(s) may be caused to stop growing and/or to stop dividing.

Whereas, through exposure of the predetermined bioactive frequency and/or waveform of electromagnetic energy and/or acoustic energy that induces the particular cellular outcome/behavior, the desired cell(s) may be caused to grow and/or divide.

A cornerstone of this technology is that a given first cell type (e.g., a certain cancer cell type—e.g., a prostate cancer cell) may respond differently than a second cell type (e.g., a healthy non-cancerous cell—e.g., a normal/healthy prostate cell) to the exact same frequency and/or waveform of electromagnetic energy and/or acoustic energy. This permits the in vivo and mildly or non-invasive selective and specific targeting of a particular cell type for a particular cellular outcome/behavior, without inducing that cellular outcome/behavior in cells of different types.

And note, the bioactive frequencies and/or bioactive waveforms of electromagnetic energy and/or of acoustic energy that the electro medical tool, the sensor tool, the treatment tool, the systems thereof, and/or the methods of using such tool(s) concerns themselves with, is not the previously known high energy applications that results in indiscriminate cell death/cooking, irrespective of cell type. For example, UV sterilization, radiation sterilization, cancer radiation therapy, and microwave cooking are all high energy applications that result in indiscriminate cell death/cooking, irrespective of cell type.

It is an objective of the present invention to provide a means to determine frequencies and/or waveforms of electromagnetic energy and/or acoustic energy that may be bioactive, resulting in and/or inducing a particular and reproducible cellular outcome/behavior in a particular type of cell.

It is another objective of the present invention to provide a means to determine frequencies and/or waveforms of electromagnetic energy and/or acoustic energy that may be bioactive, resulting in and/or inducing a particular and reproducible cellular outcome/behavior in a particular type of cell without resulting in and/or inducing that particular cellular outcome/behavior in a different particular type of cell.

It is another objective of the present invention to provide an electro medical tool for determining the bioactive frequencies and/or waveforms of electromagnetic energy and/or acoustic energy, resulting in and/or inducing a particular and reproducible cellular outcome/behavior in a particular type of cell without resulting in and/or inducing that particular cellular outcome/behavior in a different particular type of cell.

It is another objective of the present invention to provide an electro medical tool for use in vitro settings.

It is another objective of the present invention to provide a sensor tool for determining the frequencies and/or waveforms of electromagnetic energy and/or acoustic energy that may be bioactive, resulting in and/or inducing a particular and reproducible cellular outcome/behavior in a particular type of cell without resulting in and/or inducing that particular cellular outcome/behavior in a different particular type of cell.

It is another objective of the present invention to provide a sensor tool for use in mildly invasive in vivo settings.

It is another objective of the present invention to provide a treatment tool for transmitting the determined bioactive frequencies and/or waveforms of electromagnetic energy and/or acoustic energy to region of treatment, wherein at least one cell selected from the region of treatment may result in and/or may be induced into a particular and reproducible cellular outcome/behavior without resulting in and/or inducing that particular cellular outcome/behavior in a different particular type of cell of the region of treatment.

It is another objective of the present invention to provide a treatment tool that may be used in vivo and non-invasively.

It is another objective of the present invention to provide a treatment tool for treating at least one undesired cell type with outputted determined bioactive frequencies and/or waveforms of electromagnetic energy and/or acoustic energy for a particular outcome/behavior (e.g., death/destruction of the undesired cell) in the so treated at least one undesired cell type.

It is another objective of the present invention to provide a treatment tool for treating at least one cancer cell type with outputted determined bioactive frequencies and/or waveforms of electromagnetic energy and/or acoustic energy for a particular outcome/behavior (e.g., cancer cell death) in the so treated at least one cancer cell type.

It is yet another objective of the present invention to provide a treatment tool for treating at least one desired cell type with outputted determined bioactive frequencies and/or waveforms of electromagnetic energy and/or acoustic energy for a particular outcome/behavior (e.g., desired cell growth and/or division) in the so treated at least one desired cell type.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

FIG. 12A depicts part 1 of Table 1 and FIG. 12B depicts part 2 of Table 1. Table 1 depicts some determined bioactive electromagnetic frequencies and associated/or characteristics for some cell types. Note Table 1 is included in the figures (FIG. 12A and FIG. 12B) and in the patent specification.

Figure 1:
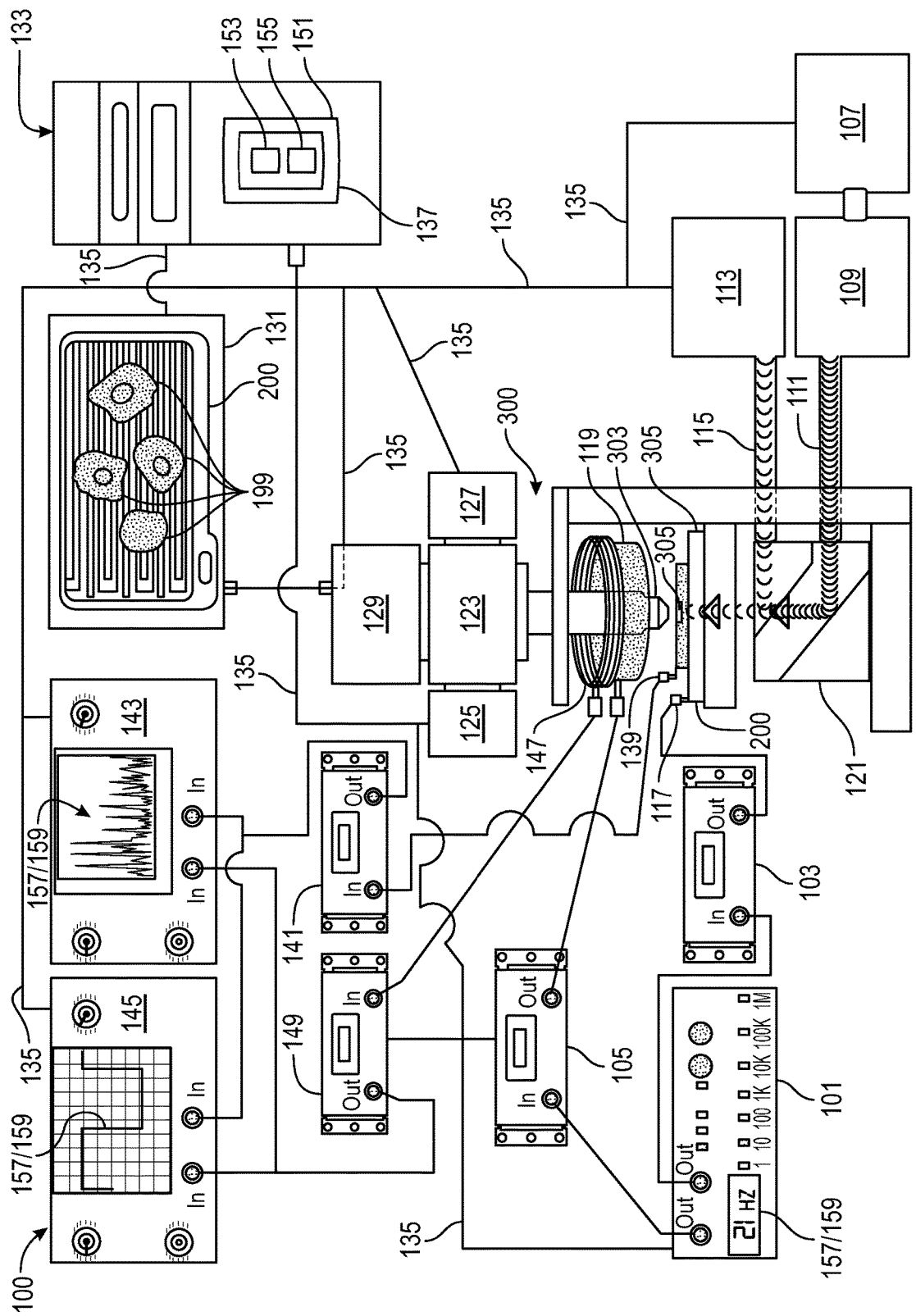
FIG. 1 may be a schematic block diagram illustrating an electro medical tool used to determine bioactive electromagnetic frequencies and associated characteristics (e.g., waveform) for a given and/or predetermined type of cell(s) and/or tissue.

REFERENCE NUMERAL SCHEDULE 100 electro medical tool 100 (determination tool 100)
101 frequency/waveform generator 101
103 power amplifier 103
105 power amplifier 105
107 white light source 107
109 monochromator 109
111 light wavelength 111
113 variable color light source 113
115 color wavelength 115
117 input conductive trace/electrode 117
119 transmitter (transducer, antenna, coil,) 119
121 dual beam combiner 121
123 splitter 123
125 wavelength meter 125
127 optical power meter 127
129 camera 129
131 video display 131
133 computer 133
135 interface 135
137 database 137
139 output conductive trace/electrode 139
141 amplifier 141
143 spectrum analyzer 143
145 oscilloscope 145
147 pickup/receiver 147
149 amplifier 149
151 software 151
153 baseline cellular info 153
155 changed cellular info 155
157 waveform 157
159 harmonic 159
199 living cell(s)/tissue 199
200 slide 200
201 conductive trace/electrode 201
300 microscope 300
301 microscope head 301
303 lens 303
305 stage 305
900 sensor tool 900
901 needle 901
903 sidewall 903
905 tip/opening 905
907 lumen 907
909 lead/electrode 909
909a hot lead 909a
909b ground 909b
911 amplifier 911
913 A to D converter 913
915 transmitter 915
917 amplifier 917
919 frequency/waveform generator 919
933 computer 933
951 software 951
999 region of tissue 999
1000 treatment tool 1000
1001 transmitter assembly 1001
1001a coil 1001a
1001b coil 1001b
1003 bobbin 1003
1003 bobbin 1003b
1003b bobbin 1003b
1005 antenna tuner 1005
1007 attenuator 1007
1009 broadband power amplifier 1009
1011 frequency Generator/waveform Generator 1011
1033 computer 1033
1037 database 1037
1051 software 1051
1099 region being treated 1099
1100 cancer treatment method 1100
1101 step of positioning region being treated between coils 1101
1103 step of generating bioactive frequency/waveform 1103

1105 step of communicating bioactive frequency/waveform 1105
1107 step of transmitting bioactive frequency/waveform to region being treated 1107
1109 step of rotating region being treated with respect to coils 1109
1111 step of administering chemotherapy 1111
1113 step of determining treatment effectiveness 1113
1115 step of updating database 1115
1117 step of selecting bioactive frequency/waveform 1117
1119 step of determining type of cancer 1119
1121 step of determining bioactive frequency/waveform 1121

DETAILED DESCRIPTION OF THE INVENTION

Note, the term of "electromagnetic energy and its particular characteristics" (such as, but not limited to, frequency, waveform, harmonics, and/or the like), as used herein may be selected from the electromagnetic spectrum and/or from the sound spectrum (e.g., acoustic and/or ultrasound).

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

With respect to relationships between the figures, note that FIG. 2, FIG. 3A, FIG. 3B, and FIG. 4 may all show aspects of an electro medical tool 100 of FIG. 1. Whereas, FIG. 9 may show a different tool as compared to FIG. 1, but wherein the FIG. 9 tool may accomplish the same or similar functions as the FIG. 1 tool, e.g., scanning and monitoring to determine bioactive electromagnetic frequencies and associated characteristics (e.g., waveform) for a given and/or predetermined type of cell(s) and/or tissue. And FIG. 10 may show another entirely different tool (e.g., different from FIG. 1 and different from FIG. 9) that may apply the previously determined bioactive frequencies and/or characteristics thereof (learned from the FIG. 1 tool and/or from the FIG. 9 tool) to a given and/or predetermined type of cell(s) and/or tissue for a particular outcome.

FIG. 1 may be a schematic block diagram illustrating electro medical tool 100 used to determine bioactive electromagnetic frequencies and associated characteristics (e.g., waveform) for a given and/or predetermined type of cell(s) and/or tissue 199. Note, the reference arrow for electro medical tool 100 in FIG. 1 is pointing to the entirety of components shown in FIG. 1.

In a nutshell, electro medical tool 100 may apply electromagnetic energy (and/or acoustic energy) of predetermined characteristics to a sample of live cell(s) 199 and electro medical tool 100 may monitor how that sample of cells 199 behaves from being dosed/exposed by that particular event electromagnetic energy exposure. In some embodiments, electro medical tool 100 may also document (e.g., in a database 137) what particular outputted electromagnetic energy results in a given outcome/behavior with respect to the dosed sample of cell(s) 199.

Using electro medical tool 100 it has been found that particular outputted electromagnetic energy results in a given outcome/behavior with respect to a particular type of living cell(s)/tissue 199; whereas, other particular outputted electromagnetic energy has no to negligible effect with respect to the same type of dosed cell(s)/tissue 199. And by using electro medical tool 100, it has been found that different types of cells/tissue 199, respond very differently to a given same dosing of particular electromagnetic energy.

Thus, electro medical tool 100 may be used to determine bioactive frequencies and/or electromagnetic characteristics that result in a given outcome/behavior for a particular type of living cell/tissue 199. That is, electro medical tool 100 may be a determination tool 100; i.e., a tool for determining those bioactive frequencies and/or electromagnetic characteristics, as not all frequencies and/or electromagnetic characteristics are bioactive for a given type of living cell/tissue 199.

The electromagnetic characteristics that may be generated, varied, controlled, and applied from electro medical tool 100 to a given set of living cell(s)/tissue 199 may comprise: frequency (or wavelength) (selected from the entire electromagnetic spectrum and/or from the acoustic spectrum); waveform (e.g., DC, sine, square, sawtooth, rising, falling, inversions, amplitude variance, gain, duty cycle variance, and/or the like); harmonic(s) of a given waveform; energy level applied; duration of exposure (e.g., in milliseconds [or other unit of time]); portions thereof; combinations thereof; and/or the like.

However, in general electromagnetic energy that is high/strong enough to be outright thermally destructive for most cell types is not of interest—as that level of energy is non-discriminative. For example, electromagnetic energy that is high/strong enough to boil cytoplasm (water) and/or outright denature substantially all/most proteins and/or denature all/most genetic nucleic acids for most cell types are not of interest. Rather, we are interested in electromagnetic energy of particular characteristics that induces a particular cellular outcome/behavior for a given type of cells/tissues 199, but that has no to negligible effect on other types of cells/tissues 199, as this may form a basis for a substantially non-invasive therapeutic treatment tool (see e.g., FIG. 10).

The cellular outcomes/behaviors that may be induced by dosing/exposing a given living cell(s)/tissue with electromagnetic energy of a predetermine characteristic may comprise: cell cycle initiation (inducement of mitosis and/or meiosis); cell growth/expansion; cell collapse/shrinkage; cell movement (e.g., increase or decrease); cell cycle arrest (cessation of mitosis and/or meiosis); cell death (e.g., apoptosis and/or necrosis); changes in cell membrane permeability; increased cell membrane permeability; decreased cell membrane permeability; cellular/membrane protein misfolding (partial protein denaturation); changes in cellular morphology; changes in cell wall (for a cell with a cell wall); cellular destruction; cell membrane rupture; portions thereof; combinations thereof; and/or the like.

As used herein, "living cell(s)/tissue 199" may refer to at least one cell that will be, is, and/or that was tested using electro medical tool 100. Before testing with electro medical tool 100, living cell(s)/tissue 199 is/are alive and/or living; however, during testing with electro medical tool 100 and/or after testing with electro medical tool 100, one or more cells from living cell(s)/tissue 199 may die (e.g., as a result of the testing/exposure). In some embodiments, living cell(s)/tissue 199 may be selected from one or more of: at least one living cell; a single cell; a plurality of cells; a single cell organism; at least one cell from a multicellular group within an organism; at least one cell selected from a predetermined cellular tissue; at least a section, region, and/or portion of cellular tissue; at least one cell of a particular and/or a predetermined type; at least one healthy cell; at least one unhealthy cell; at least one diseased cell; at least one cancerous cell; at least one cell from a tumor; at least one cell from a benign tumor; at least one cell from a malignant tumor; at least one cell of a particular and/or a predetermined genotype; at least one cell of a particular and/or a predetermined phenotype; at least one cell of a particular and/or a predetermined cell line; at least one infected cell; at least one bacterial cell; at least one eukaryotic cell; at least one fungal cell; at least one plant/algae cell; at least one animal cell; at least one vertebrate cell; at least one mammalian cell; at least one human cell; at least one marked/tagged cell; at least one hybrid cell; at least one human-made cell; at least one manufactured cell; at least one cell that does not exist in nature; at least one cell that does not exist naturally; portions thereof; combinations thereof; and/or the like.

In some embodiments, living cell(s)/tissue 199 may be a sample of region of tissue 999. In some embodiments, region of tissue 999 may be one or more cells selected from a multicellular organism but not removed from that multicellular organism; whereas, living cell(s)/tissue 199 may be removed from the given organism. In some embodiments, living cell(s)/tissue 199 may be tested with electro medical tool 100 (see e.g., FIG. 1); whereas region of tissue 999 may be tested with sensor tool 900 (see e.g., FIG. 9). In some embodiments, testing of living cell(s)/tissue 199 with electro medical tool 100 may be in vivo or in vitro, depending upon the nature the cell(s) of living cell(s)/tissue 199 (e.g., if living cell(s)/tissue 199 is a single cellular organism then its testing with electro medical tool 100 may be in vivo; whereas, if living cell(s)/tissue 199 is removed from an organism or a cell line or the like, then its testing with electro medical tool 100 may be in vitro). Whereas, in some embodiments, testing of region of tissue 999 with sensor tool 900 may be an in vivo use/application.

Continuing discussing FIG. 1, electro medical tool 100 may comprise five main means, each for accomplishing a particular goal: (1) a means for generating electromagnetic energy of a particular characteristic; (2) a means for applying that generated electromagnetic energy of a particular characteristic to a given living cell(s)/tissue 199; (3) a means for monitoring how that given living cell(s)/tissue 199 responds to being dosed with the electromagnetic energy of the particular characteristic; (4) a validation means for validating the electromagnetic energy of the particular characteristic used in a given dosing; and (5) a documenting means for documenting which electromagnetic energy of a particular characteristic may be linked with a particular cellular outcome/behavior. In some embodiments, electro medical tool 100 may also comprise various control means.

Continuing discussing FIG. 1, in some embodiments, the means for generating electromagnetic energy of the particular characteristic may comprise one or more of: frequency/waveform generator 101, power amplifier 103, power amplifier 105, white light source 107, monochromator 109, variable color light source 113, portions thereof, combinations thereof, and/or the like.

Continuing discussing FIG. 1, in some embodiments, frequency/waveform generator 101 may generate a predetermined frequency selected from the electromagnetic spectrum and/or a predetermined frequency from the acoustic spectrum. In some embodiments, frequency/waveform generator 101 may generate a predetermined frequency selected from the electromagnetic spectrum other than from the visual and/or near visual spectrum (wherein visual spectrum is with respect to humans). In some embodiments, the near visual spectrum may be ultraviolet and/or infrared. In some embodiments, frequency/waveform generator 101 may have at least one output channel. In some embodiments, frequency/waveform generator 101 may have at least two output channels (e.g., one for operative connection to amplifier 103 and one for operative connection to amplifier 105). In some embodiments, frequency/waveform generator 101 may be directly operatively connected to amplifier 103 and/or to amplifier 105. In some embodiments, frequency/waveform generator 101 may have at least two output channels (e.g., one for operative connection to input conductive trace/electrode 117 and one for operative connection to transmitter 119). In some embodiments, frequency/waveform generator 101 may be directly operatively connected to input conductive trace/electrode 117 and/or to transmitter 119. In some embodiments, frequency/waveform generator 101 may generate a predetermined waveform. In some embodiments, the predetermined waveform may be one or more of: DC (direct current—a flat and steady waveform), sine, square, sawtooth, rising, falling, ramp, pulse, noise, sweep functionality, variable duty cycle, variable amplitude, variable frequency, inversions, user defined, software 151 defined, portions thereof, combinations thereof, and/or the like. In some embodiments, an output of frequency/waveform generator 101 may be designated herein as waveform 157. In some embodiments, waveform 157 may have any of the electromagnetic characteristics noted above and the given electromagnetic characteristics of waveform 157 may be predetermined. In some embodiments, a variable frequency range of frequency/waveform generator 101 may be from DC to 900 gigahertz. In other embodiments, frequency/waveform generator 101 may have a different variable frequency range. For example, the Anritsu MG3690C (or the like) with frequency extender options may cover near DC to 900 gigahertz in one unit. For the purposes of the present invention, frequency/waveform generator 101 frequency range in practice may only be limited by the current state of the art. In some embodiments, frequency/waveform generator 101 may be operatively connected to a computer 133, via an interface 135 (e.g., cabling/wiring). See e.g., FIG. 1. In some embodiments, frequency/waveform generator 101 may be operatively connected to one or more power sources (not shown in FIG. 1).

Continuing discussing FIG. 1, in some embodiments, output(s) of frequency/waveform generator 101 (e.g., waveform 157) may be operationally linked/coupled to amplifier 103 and/or to amplifier 105. In some embodiments, amplifier 103 and/or amplifier 105 may be wideband power amplifier(s). In some embodiments, amplifier 103 may have a frequency response at least equal to an output from frequency/waveform generator 101. In some embodiments, amplifier 103 may be operationally connected to input conductive trace/electrode 117. In some embodiments, amplifier 105 may have a frequency response at least equal to an output from frequency/waveform generator 101. In some embodiments, amplifier 105 may be operationally connected to transmitter 119. See e.g., FIG. 1.

Continuing discussing FIG. 1, in some embodiments, white light source 107 may generate visible white light (wherein visible may be with respect to humans). In some embodiments, white light source 107 may be operationally linked/coupled to monochromator 109. In some embodiments, white light source 107 and/or monochromator 109 may output visible light 111 of a predetermined spectrum (wavelength). In some embodiments, monochromator 109 may be capable of splitting a white light source 107 into single nanometer or sub nanometer wavelengths 111 that may range from 200 to 1100 nanometers (nm), but said wavelengths 111 in practice may only be limited by the state of the art in monochromator 109 technology. In some embodiments, monochromator 109 may output any of said wavelengths 111 through any cell of living cell(s)/tissue 199 and on through/into a lens 303 of a microscope 300. In some embodiments, monochromator 109 may be operated manually and/or may be electrically coupled to computer 133 which may be configured and/or operated with/by software 151. In some embodiments, software 151 may be configured to direct/operate/control monochromator 109 to provide desired specific wavelengths 111. See e.g., FIG. 1.

Continuing discussing FIG. 1, in some embodiments, variable color light source 113 may generate visible light of a predetermined color (wherein visible may be with respect to humans). In some embodiments, variable color light source 113 may output visible colored light 115 of a predetermined spectrum (wavelength). In some embodiments, variable color light source 113 may be configured to output any one or more of millions or billions of colors 115; wherein said colors 115 in practice may only be limited by the state of the art in computer software and variable color light source 113 technology. In some embodiments, variable color light source 113 may be configured to output said colors 115 through any cell of living cell(s)/tissue 199 and on through/into lens 303 of microscope 300. In some embodiments, variable color light source 113 may be a video projector, an RGB (red, green, blue) color laser array, a super continuum laser, an LED (light emitting diode), or any other variable color emitting light source that derives its color output commands manually by a user and/or from software 151 running on computer 133. In some embodiments, software 151 may be configured to control variable color light source 113 that is electrically coupled to computer 133. See e.g., FIG. 1.

Continuing discussing FIG. 1, in some embodiments, white light source 107, monochromator 109, and/or variable color light source 113 may generate from ultraviolet light to infrared light. In some embodiments, white light source 107, monochromator 109, and/or variable color light source 113 may generate visible light (wherein visible may be with respect to humans). In some embodiments, white light source 107, monochromator 109, and/or variable color light source 113 may be configured to emit light of a predetermined wavelength(s) onto the given sample of cell(s)/tissue 199. In some embodiments, white light source 107, monochromator 109, and/or variable color light source 113 may be configured to emit light of a predetermined wavelength(s) onto a dual beam combiner 121, wherein an output from the dual beam combiner 121 may be onto the given sample of cell(s)/tissue 199. See e.g., FIG. 1.

In some embodiments, a user may manually choose to lock-in or sweep through the light wavelength 111 outputs of monochromator 109 and/or of variable color source 113 colors 115 (so as to expose cell(s)/tissue 199 to a variety of light wavelengths 111 and/or colors 115). In some embodiments, software 151 may be configured to sweep through and lock in any wavelength(s) 111 or colors 115 of light, or combinations of the light outputs of monochromator 109 and variable color source 113 at a particular sweep rate not to exceed the image and data acquisition limits of a camera 129. (In some embodiments, camera 129 may be a component of microscope 300 or may be an accessory/attachment to microscope 300.)

Continuing discussing FIG. 1, in some embodiments, the means for applying that generated electromagnetic energy of the particular characteristic to a given living cell(s)/tissue 199 may comprise: input conductive trace/electrode 117, transmitter 119, dual beam combiner 121, light wavelength 111, colors 115, portions thereof, combinations thereof, and/or the like.

Continuing discussing FIG. 1, in some embodiments, frequency/waveform generator 101 may be operatively linked to input conductive trace/electrode 117. In some embodiments, frequency/waveform generator 101 may be operatively linked to power amplifier 103. In some embodiments, power amplifier 103 may be operatively linked to input conductive trace/electrode 117. In some embodiments, input conductive trace/electrode 117 may be an input conductive trace mounted to (attached to) a surface of a given slide 200, wherein slide 200 may receive living cell(s)/tissue 199. In some embodiments, slide 200 may be a microscope slide (including a slide for microscope 300). In some embodiments, slide 200 may be at least substantially optically clear, transparent, and/or translucent. In some embodiments, at least a portion of the living cell(s)/tissue 199 may reside on top of input conductive trace/electrode 117 on slide 200. In some embodiments, slide 200 may have an input conductive trace/electrode 117, wherein input conductive trace/electrode 117 may be electrically connected to wideband power amplifier 103 and/or to frequency/waveform generator 101. See e.g., FIG. 1.

Continuing discussing FIG. 1, in some embodiments, frequency/waveform generator 101 may be operatively linked to transmitter 119. In some embodiments, frequency/waveform generator 101 may be operatively linked to power amplifier 105. In some embodiments, power amplifier 105 may be operatively linked to transmitter 119. In some embodiments, frequency/waveform generator 101 may be electrically coupled directly to electromagnetic field output transducer 119 by bypassing amplifier 105. In some embodiments, transmitter 119 may be configured to transmit/emit electromagnetic energy of a predetermined characteristic, such as, but not limited to, waveform 157. In some embodiments, transmitter 119 may be an antenna, a transducer, a coil of conductive material, portions thereof, combinations thereof, and/or the like. In some embodiments, such a coil may have predetermined quantity of turns and its conductive materials may be predetermined. In some embodiments, transmitter 119 may be one or more electromagnetic field output transducers. In some embodiments, electromagnetic field output transducer 119 may be a single transducer or a plurality of transducers configured to generate an electromagnetic field in response to any waveform 157 provided by frequency/waveform generator 101. In certain frequency ranges, electromagnetic field output transducer 119 may be a waveguide as shown in FIG. 3B. In some embodiments, electromagnetic field output transducer 119 may have frequency response at least equal to an output from frequency/waveform generator 101 (e.g., waveform 157). In some embodiments, transmitter 119 and pickup/receiver 147 may be mounted concentrically and linearly with respect to each other. In some embodiments, transmitter 119 may be positioned proximately, but not physically touching living cell(s)/tissue 199. In some embodiments, transmitter 119 may be a coil around a distal/terminal lens portion of a given microscope head 301 (as this may position transmitter 119 proximate to living cell(s)/tissue 199). In some embodiments, transmitter 119 may be a coil around a distal/terminal lens portion of a given lens 303 (as this may position transmitter 119 proximate to living cell(s)/tissue 199). In some embodiments, electromagnetic field output transducer 119 may have a frequency response at least equal to outputs of frequency/waveform generator 101. See e.g., FIG. 1.

Continuing discussing FIG. 1, in some embodiments, white light source 107, monochromator 109, and/or variable color light source 113 may be operatively linked to dual beam combiner 121. In some embodiments, dual beam combiner 121 may be configured to emit light of a predetermined wavelength onto living cell(s)/tissue 199. In some embodiments, dual beam combiner 121 may be used to combine and aim the light outputs (e.g., light wavelength 111 and/or color 115) from monochromator 109 and variable color light source 113 through any cell of living cell(s)/tissue 199. In some embodiments, dual beam combiner 121 may combine outputs (light wavelength 111 and/or color wavelength 115) from white light source 107, monochromator 109, and/or from variable color light source 113. In some embodiments, dual beam combiner 121 may permit only one output (light wavelength 111 or color wavelength 115) from white light source 107, monochromator 109, or from variable color light source 113. See e.g., FIG. 1.

Continuing discussing FIG. 1, in some embodiments, the means for monitoring how the given living cell(s)/tissue 199 responds to being dosed with the electromagnetic energy of the particular characteristic (e.g., waveform 157) may occur on at least two different fronts: (1) visually via high-resolution microscopy (such as, but not limited to, using at least one microscope 300, MRI, CT scan, ultrasound imaging, and/or the like); (2) by monitoring electrical changes in the given living cell(s)/tissue 199 (e.g., using output trace(s)/electrode(s) 139, EEG outputs, and/or the equivalents); and/or (3) by monitoring molecular changes in the given living cell(s)/tissue 199 using broadband infrared spectroscopy (Fourier Transform Infrared Spectroscopy [FTIR]), Raman spectroscopy, and/or the like (e.g., using pick-ups/receivers 147). In some embodiments, being able to derive and/or determine the bioactive frequencies, signals, and/or associated electromagnetic characteristics, depends, at least in part, on being able to observe and/or monitor how the given living cell(s)/tissue 199 (and/or portion thereof) may change and/or respond from a given dosing event(s) of the predetermined electromagnetic energy and its predetermined characteristics (e.g., waveform 157). In some embodiments, the means for monitoring may comprise one or more feedback loops, such as, but not limited to: (1) observing physical changes in the given living cell(s)/tissue 199 (or portion thereof) by using high-resolution microscopy, MRI, CT scan, ultrasound imaging, and/or the like; (2) observing electrical changes via use of electrodes (e.g., output trace(s)/electrode(s) 139 and/or sensor tool 900) in the given living cell(s)/tissue 199 (or portion thereof); (3) observing molecular changes in the given living cell(s)/tissue 199 (or portion thereof) (e.g., using FTIR spectroscopy, Raman spectroscopy, and/or the like facilitated by using pick-ups/receivers 147); and/or the like. In some embodiments, the high-resolution microscopy, MRI, CT scan, ultrasound imaging, and/or the like, may be done in vitro and/or in vivo. In some embodiments, the use of electrodes and/or the like, may be done in vitro and/or in vivo. In some embodiments, the use of FTIR spectroscopy, Raman spectroscopy, and/or the like, may be done in vitro and/or in vivo (e.g., on a living tissue sample through biopsy and/or surgical excision of such living tissue).

Continuing discussing FIG. 1, in some embodiments, electro medical tool 100 may comprise at least one microscope 300. In some embodiments, microscope 300 may be positioned and/or configured to visually monitor and/or observe the living cell(s)/tissue 199 (on slide 200). In some embodiments, microscope 300 may comprise a microscope head 301 with at least one lens 303; and may further comprise one or more of: a (beam) splitter 123, a wavelength meter 125, an optical power meter 127, a camera 129, a video display 131, stage 305, portions thereof, combinations thereof, and/or the like. In some embodiments, lens 303 may be in communication with splitter 123. In some embodiments, wavelength meter 125 and/or optical power meter 127 may be installed on beam splitter 123 on microscope 300 to log and/or record the spectral/electromagnetic information of the living cell(s)/tissue 199 before and/or after dosing/exposure with the generated electromagnetic energy of the particular characteristics (e.g., waveform 157) from frequency/waveform generator 101. In some embodiments, wavelength meter 125 and optical power meter 127 may be a single spectrometer device incorporating functions of both units. In some embodiments, wavelength meter 125 and/or optical power meter 127 may be components of computer 133. In some embodiments, wavelength meter 125 and/or optical power meter 127 may have a same frequency response as monochromator 109 and/or as variable color light source 113. In some embodiments, wavelength meter 125 and/or optical power meter 127 may have a same frequency response as an output from frequency/waveform generator 101 (such as, but not limited to, waveform 157). In some embodiments, wavelength meter 125 and/or optical power meter 127 may be operatively coupled to computer 133 through instrument interface 135 and information they (wavelength meter 125 and/or optical power meter 127) provide may continually populate relevant fields in database 137. In some embodiments, splitter 123 may be in communication with camera 129. In some embodiments, camera 129 may be mounted on splitter 123 of microscope 300 so as to view the living cell(s)/tissue 199 through lens 303. In some embodiments, camera 129 may be operatively connected to at least one video display 131. In some embodiments, video display 131 may be configured to display images and/or video of the living cell(s)/tissue 199 on/from slide 200 captured by camera 129 coupled to/with lens 303 that may be focused on slide 200 or portion thereof. In some embodiments, video display 131 may be coupled to a video output of camera 129 to allow a user to monitor any effect of frequency/waveform generator 101 outputted waveform 157 on any cell of living cell(s)/tissue 199. In some embodiments, an output from camera 129 and/or from video display 131 may be electrically coupled to computer 133 through instrument interface 135. In some embodiments, software 151 may be configured to track and map any cell 15 of living cell(s)/tissue 199 and populate database 137 with cell size and cell mechanics data derived from image data provided by camera 129 and/or from microscope 300 image data. In some embodiments, software 151 may be configured to detect any cellular behavior alteration 155 from camera 129 and/or from microscope 300. In some embodiments, software 151 may be configured to detect cellular behavior alteration 155 from camera 129 and/or from microscope 300 above a predetermined threshold as compared to baseline cellular characteristics/information 153. In some embodiments, cellular behavior alteration 155 may be mapped by software program 151 in response to image data derived from camera 129 and/or from microscope 300. In some embodiments, cellular behavior alteration 155 may include any cell behavior deviation from a baseline cell behavior information 153, including, but not limited to, changes in size and/or shape of a given cell of living cell(s)/tissue 199. In some embodiments, baseline cell behavior information 153 may be refreshed with respect to initial living cell(s)/tissue 199 size data at a start of every experiment/test. In some embodiments, as camera 129 and/or microscope 300 image data updates database 137, cellular behavior alteration 155 data may enable software 151 to track hundreds or thousands of cells in a given sample of cell living cell(s)/tissue 199 simultaneously. In some embodiments, video display 131 may be an output device of computer 133. In some embodiments, video display 131 may be operatively connected to computer 133 (e.g., via instrument interface 135). See e.g., FIG. 1.

Continuing discussing FIG. 1, in some embodiments, a surface of slide 200 may comprise at least one output conductive trace/electrode 139. In some embodiments, at least a portion of the living cell(s)/tissue 199 may reside on top of output conductive trace/electrode 139. In some embodiments, output conductive trace 139 and input conductive trace 117 may not intersect nor directly physically contact each other. In some embodiments, output conductive trace/electrode 139 may be operatively linked/coupled to amplifier 141. In some embodiments, amplifier 141 may have a frequency response at least equal to an output from frequency/waveform generator 101. In some embodiments, amplifier 141 may be operatively linked/coupled to spectrum analyzer 143 and/or to oscilloscope 145. In some embodiments, amplifier 141 outputs may be electrically coupled in parallel to oscilloscope 145 input channel and to spectrum analyzer 143 input channel. In this way, output conductive trace/electrode 139, via spectrum analyzer 143 and/or via oscilloscope 145, may be used to monitor the electromagnetic profile of the living cell(s)/tissue 199. In some embodiments, output conductive trace/electrode 139 may be used to monitor impedance changes of the living cell(s)/tissue 199. In some embodiments, amplifier 141 may eliminate/reduce impedance mismatches in the living cell(s)/tissue 199 as any electromagnetic energy of a particular characteristic (e.g., waveform 157) may be applied to traces 117 and 139 from waveform generator 101 through power amplifier 103. See e.g., FIG. 1.

Continuing discussing FIG. 1, in some embodiments, electro medical tool 100 may comprise at least one pickup/receiver 147. In some embodiments, pickup/receiver 147 may be one or more of an antenna, a transducer, a pickup, a receiver, a coil, portions thereof, combinations thereof, and/or the like. In some embodiments, pickup/receiver 147 may be configured to receive electromagnetic energy of a particular characteristic from the living cell(s)/tissue 199. In some embodiments, electromagnetic pickup transducer 147 may be a single transducer or a plurality of transducers configured to sense an electromagnetic field in response to any waveform 157 provided by frequency/waveform generator 101. In some embodiments, predetermined/certain frequency ranges electromagnetic pickup transducer 147 may be a waveguide as shown in FIG. 3B. In some embodiments, pickup/receiver 147 may be a coil around a distal/terminal lens portion of a given microscope head 301 (as this may position pickup/receiver 147 proximate to living cell(s)/tissue 199). In some embodiments, pickup/receiver 147 may be a coil around a distal/terminal lens portion of lens 303 (as this may position pickup/receiver 147 proximate to living cell(s)/tissue 199). In some embodiments, pickup/receiver 147 may be positioned to be proximate to the living cell(s)/tissue 199; however pickup/receiver 147 may be further away from the living cell(s)/tissue 199 as compared to transmitter 119. In some embodiments, pickup/receiver 147 may be operatively linked/coupled to amplifier 149. In some embodiments, amplifier 149 may be operatively linked/coupled to spectrum analyzer 143 and/or to oscilloscope 145. In this way, pickup/receiver 147, via spectrum analyzer 143 and/or via oscilloscope 145, may be used to monitor the electromagnetic profile of the living cell(s)/tissue 199. In some embodiments, pickup/receiver 147 may be used to monitor impedance and/or amplitude changes of the living cell(s)/tissue 199. In some embodiments, amplifier 149 may eliminate/reduce impedance mismatches in the living cell(s)/tissue 199 as any electromagnetic energy of a particular characteristic may be applied to transmitter 119 and pickup/receiver 147 from waveform generator 101 through power amplifier 105. See e.g., FIG. 1.

Continuing discussing FIG. 1, in some embodiments, the validation means for validating the electromagnetic energy of the particular characteristic (e.g., waveform 157) used in dosing/exposing the living cell(s)/tissue 199, may verify that the electromagnetic energy of the particular characteristic (e.g., waveform 157) is being used (or was used) to dose the living cell(s)/tissue 199. In some embodiments, the validation means for validating the electromagnetic energy of the particular characteristic (e.g., waveform 157) used in dosing the living cell(s)/tissue 199, may verify how the living cell(s)/tissue 199 are responding (or have responded to) that the electromagnetic energy of the particular characteristic (e.g., waveform 157) that is/was used to dose the living cell(s)/tissue 199. In some embodiments, the validation means for validating the electromagnetic energy of the particular characteristic (e.g., waveform 157) used in dosing the living cell(s)/tissue 199 may utilize one or more of: spectrum analyzer 143, oscilloscope 145, screen(s) of frequency/waveform generator 101, screen(s) of amplifier 103, screen(s) of amplifier 105, screen(s) of amplifier 141, screen(s) of amplifier 149, video display 131, software 151, portions thereof, combinations thereof, and/or the like. The various screens and/or displays may display what electromagnetic energy of the particular characteristic (e.g., waveform 157) was and/or is being outputted by the given device/component. In some embodiments, amplifier 141 may have a frequency response at least equal to an output from frequency/waveform generator 101. In some embodiments, amplifier 149 may have a frequency response at least equal to an output from frequency/waveform generator 101. In some embodiments, spectrum analyzer 143 may be operatively connected to one or more of: amplifier 141, amplifier 149, input conductive trace/electrode 117, transmitter 119, and/or the like. In some embodiments, oscilloscope 145 may be operatively connected to one or more of: amplifier 141, amplifier 149, input conductive trace/electrode 117, transmitter 119, and/or the like. In some embodiments, oscilloscope 145 and/or spectrum analyzer 143 may each have multiple input channels. In some embodiments, oscilloscope 145 input channel and spectrum analyzer 143 input channel may be electrically coupled in parallel to an output of amplifier 141. In some embodiments, oscilloscope 145 input channel and spectrum analyzer 143 input channel may be electrically coupled in parallel to an output of amplifier 149. In some embodiments, oscilloscope 145 and spectrum analyzer 143 may have a same frequency response as frequency/waveform generator 101. In some embodiments, oscilloscope 145 and spectrum analyzer 143 may be used to make sure that any waveform 157 applied to transducer 119 are in fact reaching living cell(s)/tissue 199. In some embodiments, oscilloscope 145 and spectrum analyzer 143 may be used to make sure that any waveform 157 applied to input conductive trace/electrode 117 are in fact reaching living cell(s)/tissue 199. In some embodiments, oscilloscope 145 and spectrum analyzer 143 may be directly electrically connected to output conductive trace/electrode 139 by bypassing amplifier 141. In some embodiments, oscilloscope 145 and spectrum analyzer 143 may be directly electrically connected to transducer pickup/receiver 147 by bypassing amplifier 149. In some embodiments, oscilloscope 145 and spectrum analyzer 143 functions may be incorporated into a single spectrophotometer device. In some embodiments, oscilloscope 145 and spectrum analyzer 143 may be components of computer 133 and operated by software 151 or the like. See e.g., FIG. 1.

Continuing discussing FIG. 1, in some embodiments, computer 133 may be operatively connected to one or more of: frequency/waveform generator 101, power amplifier 103, power amplifier 105, white light source 107, monochromator 109, light wavelength 111, variable color light source 113, color wavelength 115, input conductive trace 117, transmitter (transducer, antenna, coil,) 119, dual beam combiner 121, splitter 123, wavelength meter 125, optical power meter 127, camera 129, video display 131, output conductive trace 139, conductive trace/electrode 201, amplifier 141, spectrum analyzer 143, oscilloscope 145, pickup/receiver 147, amplifier 149, inputs thereof, outputs thereof, sensors of electro medical tool 100, instruments of electro medical tool 100, devices of electro medical tool 100, components of electro medical tool 100, a network adapter/card, a network, a LAN (local area network), a WAN (wide area network), the Internet, portions thereof, combinations thereof, and/or the like. In some embodiments, the connection(s) that may enable such operative connections with/to computer 133 may be one or more interface(s) 135. In some embodiments, interface(s) 135 may be one or more wires, cables, portions thereof, combinations thereof, and/or the like. In some embodiments, interface(s) 135 may be configured for electrical and/or optical communications. In some embodiments, interface(s) 135 may be configured for power transmission, for data transmission, for control/instruction transmission, for communication, for bidirectional communications, portions thereof, combinations thereof, and/or the like. In some embodiments, these data couplings between computer 133 and other components described and noted herein may be USB, RS232, Firewire, GPIB, or any other industry standard instrumentation data interface. In some embodiments, the electrical signal couplings between components of electro medical tool 100 may be BNC cables or any other similar industry standard cable/wire.

Continuing discussing FIG. 1, in some embodiments, software 151 may be non-transitorily stored in storage (e.g., hard drive or the like) of computer 133 and called up into memory (e.g., RAM) for interactions with processor(s) of computer 133. In some embodiments, software 151 may be configured for various predetermined control, operation, monitoring, sweeps, validation, documenting, database management, portions thereof, combinations thereof, and/or like with respect to functions of electro medical tool 100 and the components of electro medical tool 100. In some embodiments, software 151 may be configured for various validation operations, including, but not limited to, polling/checking/sampling inputs and/or outputs of various sensors, feeds, devices, instruments, components, and/or the like that may be operatively connected to computer 133. In some embodiments, software 151 may be able to change the electromagnetic energy of the particular characteristics (e.g., waveform 157) that will be, and/or is to be directed at the living cell(s)/tissue 199. In some embodiments, software 151 may be able to check and/or confirm what electromagnetic energy of the particular characteristics (e.g., waveform 157) is and/or was dosed to the living cell(s)/tissue 199.

Continuing discussing FIG. 1, in some embodiments, the documenting means for documenting which electromagnetic energy of a particular characteristic (e.g., waveform 157) may be linked with a particular cellular outcome/behavior for a particular type of cell(s)/tissue 199 may be done at least in part by non-transitorily recording data into database 137. In some embodiments, computer 133 may comprise database 137. In some embodiments, computer 133 may comprise one or more storage units (e.g., hard drives or the like) wherein database 137 may reside. In some embodiments, software 151 may be configured for database management of database 137. In some embodiments, software 151 may be configured to store non-transitorily data in database 137 of one or more of: the living cell(s)/tissue 199 characteristics (e.g., cell/tissue type, cell line name(s)/nomenclature, phenotype information, genotype information, patient name and/or identifying information, and/or the like); cell counts; cell sizes; cell movements; cellular morphology; baseline (default/pre-dosing) cellular characteristics 153 of the living cell(s)/tissue 199; changes in cellular characteristics 155 (e.g., changes in cellular behavior or outcomes) of the living cell(s)/tissue 199 occurring during and/or after a particular electromagnetic energy of a particular characteristic (waveform 157) dosing event; the particular characteristics of the electromagnetic energy (waveform 157) from a given dosing event (that gave rise to a change in cellular characteristics); date and/or time stamp information; changes therein, portions thereof; combinations thereof; and/or the like.

In some embodiments, in database 137, each cell location within a given sample of living cell(s)/tissue 199 on slide 200 may be represented in/by a predetermined coordinate system. In some embodiments, the predetermined coordinate system may be a Cartesian coordinate system or the like using three orthogonal axis, such as, x, y, and z axis. (In some embodiments, the predetermined coordinate system may be used.) In some embodiments, the predetermined coordinate system may comprise an origin or "zero" point, which may be predetermined. In this way, a three-dimensional (3D) environmental location of each cell within a given sample of living cell(s)/tissue 199 on slide 200 may be known (by a user, by computer 133, by software 151, by database 137, and/or the like) and tracked over time. In some embodiments, a resolution of such a cellular location tracking system may be 0.2 microns or a resolution only limited by current state of the art in optical lens/microscope technology. This type of "object of interest" microscopic targeting and tracking software is now available from an array of software providers.

In some embodiments, any cellular behavior alteration 155 data may be logged and updated in real time (or near real time) continually updating field data in database 137 as managed by software 151. In some embodiments, an array of statistical outputs from cellular behavior alteration 155 data may include one or more of: updated position/location information of any cell of living cell(s)/tissue 199; acceleration/deceleration of any cell of living cell(s)/tissue 199; expansion/contraction (shrinkage) of any cell of living cell(s)/tissue 199; ambient fluid flow into/out of any cell of living cell(s)/tissue 199; cellular growth of any cell of living cell(s)/tissue 199; cellular morphology changes any cell of living cell(s)/tissue 199; cellular division of living cell(s)/tissue 199; cellular death of a cell of living cell(s)/tissue 199; portions thereof; combinations thereof; and/or the like—any of which in real time, near real time, and/or over time.

In some embodiments, "resonant frequencies" of a given cell(s) of living cell(s)/tissue 199 may be a subset of any available waveform 159 that resulted in a given cellular behavior/outcome change 155. In some embodiments, such resonant frequencies must initially be identified through laboratory experimentation using electro medical tool 100

(or sensor tool 900), and may then be integrated within database 137 (e.g., by using software 151) as lookup tables. In some embodiments, "overdriving" an amplitude of said resonant frequencies with respect to a base rate of frequency absorption of a given cell(s) of living cell(s)/tissue 199, said rate frequency absorption data contained in database 137, may affect the electrical conductivity, the chemical, and/or the mechanical conditions of that given cell(s) of living cell(s)/tissue 199.

Continuing discussing FIG. 1, in some embodiments, computer 133 may control, operate, and/or monitor one or more of: frequency/waveform generator 101, power amplifier 103, power amplifier 105, white light source 107, monochromator 109, light wavelength 111, variable color light source 113, color wavelength 115, input conductive trace 117, transmitter (transducer, antenna, coil,) 119, dual beam combiner 121, splitter 123, wavelength meter 125, optical power meter 127, camera 129, video display 131, output conductive trace 139, amplifier 141, spectrum analyzer 143, oscilloscope 145, pickup/receiver 147, amplifier 149, inputs thereof, outputs thereof, sensors of electro medical tool 100, instruments of electro medical tool 100, devices of electro medical tool 100, components of electro medical tool 100, memory of computer 133 (e.g., RAM), storage of computer 133 (e.g., hard drive(s) or the like), database 137, a network adapter/card of computer 133, a network in communication with computer 133, portions thereof, combinations thereof, and/or the like. In some embodiments, computer 133 may be able to control, operate, change, and/or monitor one or more of: generation of the electromagnetic energy of a particular characteristic (e.g., waveform 157); delivery of the electromagnetic energy of a particular characteristic (e.g., waveform 157); monitoring of the living cell(s)/tissue 199 (both before and after a given dosing event); validation of the generation, of the delivery, and/or of the outcome of the delivered electromagnetic energy of a particular characteristic (e.g., waveform 157) to the living cell(s)/tissue 199; documenting the generation, the delivery, and/or the outcome of the delivered electromagnetic energy of a particular characteristic to the living cell(s)/tissue 199; portions thereof; combinations thereof; and/or the like.

Continuing discussing FIG. 1, in some embodiments, electro medical tool 100 may comprise at least one (or one or more) of: frequency/waveform generator 101, power amplifier 103, power amplifier 105, white light source 107, monochromator 109, light wavelength 111, variable color light source 113, color wavelength 115, input conductive trace 117, transmitter (transducer, antenna, coil,) 119, dual beam combiner 121, splitter 123, wavelength meter 125, optical power meter 127, camera 129, video display 131, computer 133, interface(s) 135, database 137, memory of computer 133 (e.g., RAM or the like), storage of computer 133 (e.g., hard drive(s) or the like), software 151, output conductive trace 139, conductive trace/electrode 201, amplifier 141, spectrum analyzer 143, oscilloscope 145, pickup/receiver 147, amplifier 149, power supplies; inputs thereof, outputs thereof, sensors of electro medical tool 100, instruments of electro medical tool 100, devices of electro medical tool 100, components of electro medical tool 100, a network adapter/card, a network, portions thereof, combinations thereof, and/or the like.

Figure 2:
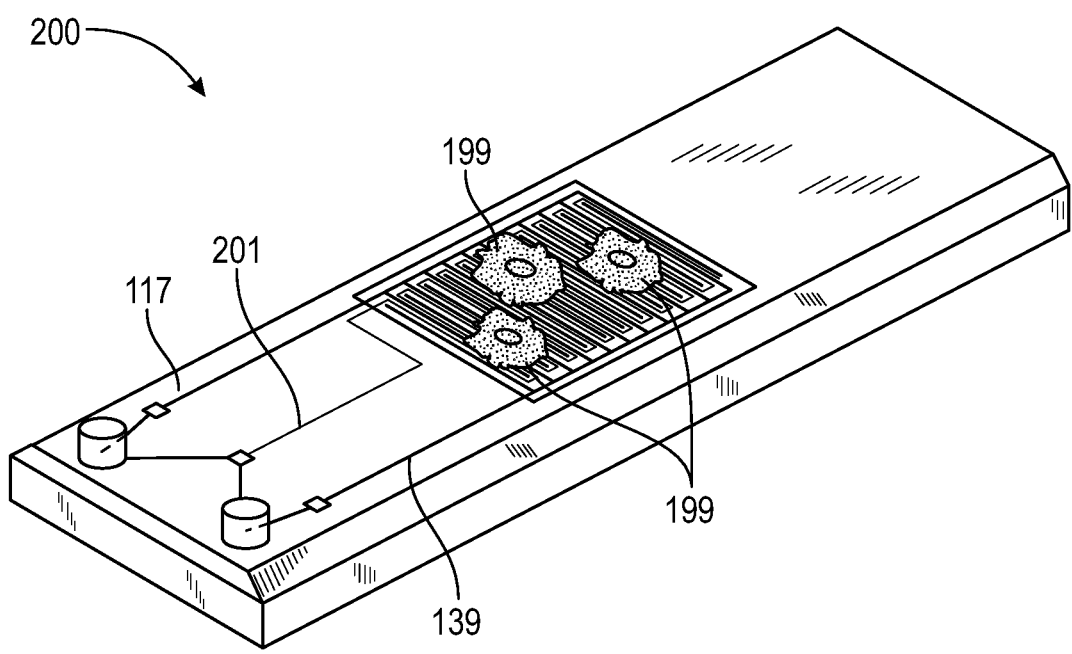
FIG. 2 may be a closer up view of a microscope slide that may house/support the given and/or the predetermined type of cell(s) and/or tissue and/or may be fitted with conductive traces/electrodes contacting the cell(s).

FIG. 2 may be a closer up view of a slide 200. In some embodiments, slide 200 may house/support the given and/or the predetermined type of cell(s) 199 and/or tissue 199. In some embodiments, slide 200 may be fitted with conductive traces/electrodes (e.g., input conductive trace 117 and output conductive trace 139) configured to physically contacting the cell(s) 199. In some embodiments, a top surface of slide 200 may comprise at least two traces/electrodes (e.g., input conductive trace 117 and output conductive trace 139). In some embodiments, a top surface of slide 200 may comprise at least three traces/electrodes of: input conductive trace 117, output conductive trace 139, and conductive trace/electrode 201. In some embodiments, conductive trace/electrode 201 may function as a ground. In some embodiments, slide 200 may be comprise a minimum of three electrically conductive traces/electrodes 117, 139, and 201. In some embodiments, slide 200 may be configured with a minimum of three electrically conductive traces/electrodes 117, 139, and 201. In some embodiments, electrically conductive traces/electrodes 117, 139, and 201 may be configured to make electrical contact with any cell of living cell(s)/tissue 199. See also FIG. 4.

Figure 3A:
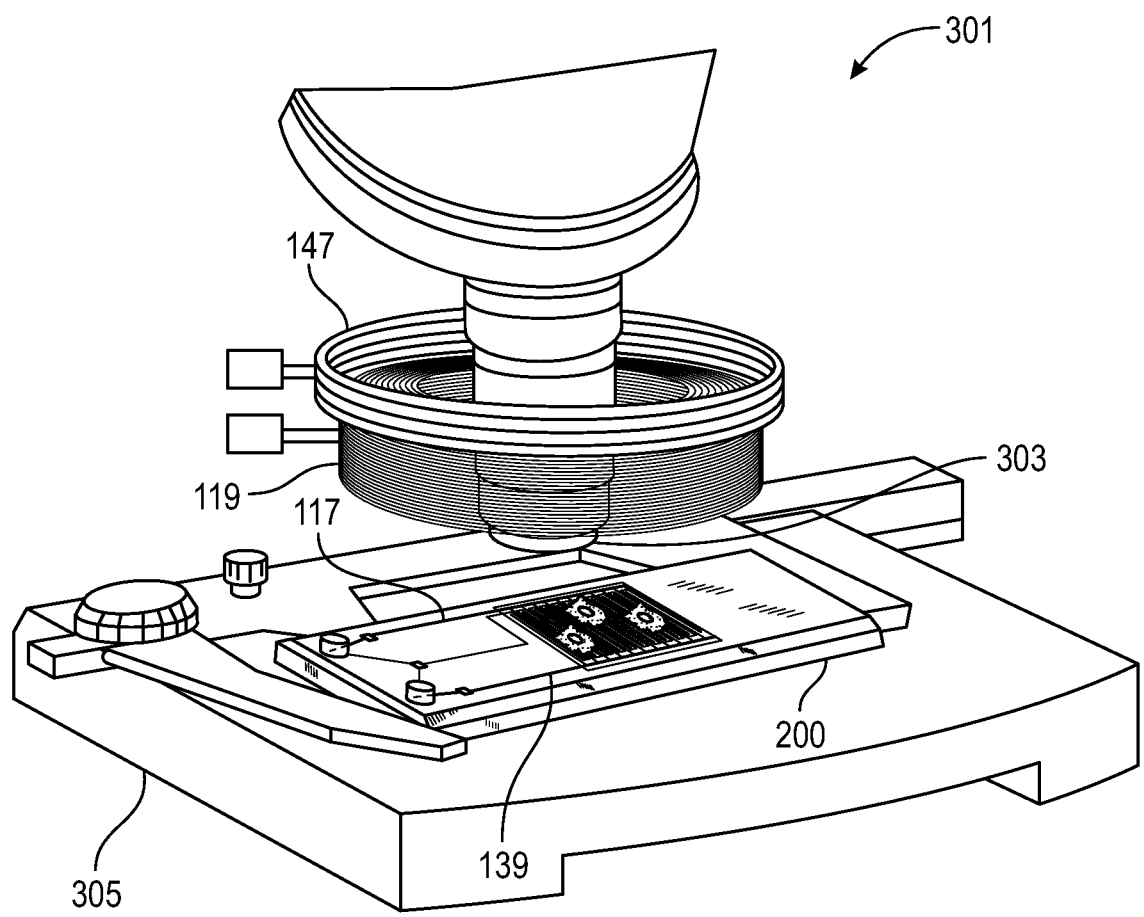
FIG. 3A may be a close up view of a microscope head fitted with transmitters (e.g., coils) and pickups/receivers (e.g., coils), and/or with a slide with conductive trace/electrodes.
Figure 3B:
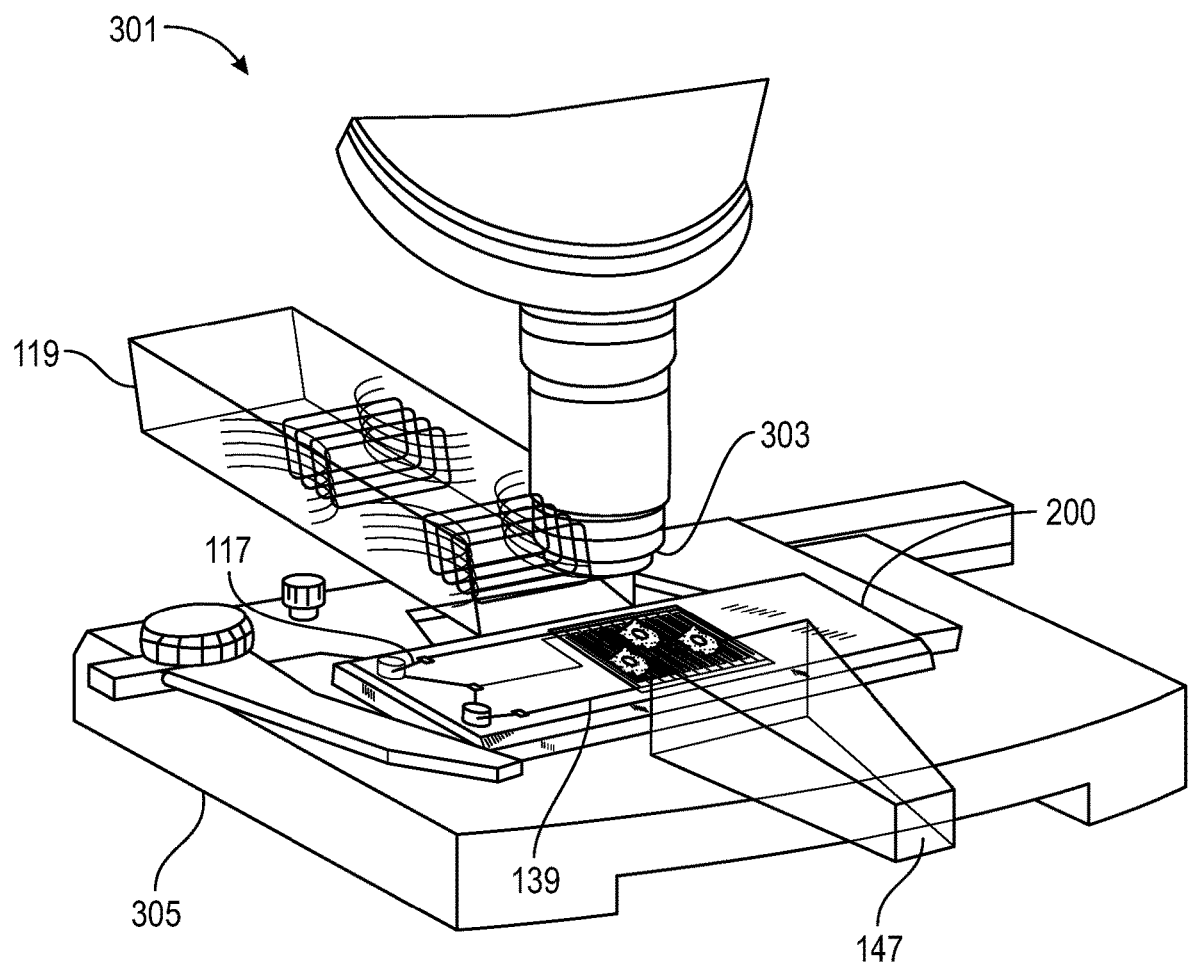
FIG. 3B may be a close up view of a microscope head fitted with a waveguide(s).

FIG. 3A may be a close up view of microscope head 301 with transmitter(s) (e.g., coil(s)) 119 and pickup(s)/receiver(s) (e.g., coil(s)) 147 located proximate to microscope head 301 and/or to lens 303. FIG. 3A may also show that a terminal/distal portion of lens 303 may be placed/located proximate to and over slide 200 and/or to the living cell(s)/tissue 199 that may be residing upon slide 200. In some embodiments, slide 200 may be resting upon stage 305 of microscope 300. In some embodiments, stage 305 may be a stage of a microscope, including that of microscope 300. In some embodiments, stage 305 may be configured to physically support at least one slide 200. In some embodiments, dual beam combiner 121 may be located below stage 305. In some embodiments, stage 305 may have opening(s) to receive outputs from dual beam combiner 121, of wavelength 111, and/or of color 115; so that these output(s) may shine onto a bottom a given slide 200.

FIG. 3B may be a close up view of a microscope head 301 fitted with at least one waveguide. In some embodiments, transmitter 119 may be configured as a waveguide. In some embodiments, pickup/receiver 147 may be configured as a waveguide. In some embodiments, transmitter 119 and/or pickup/receiver 147 may be placed/located so as to be proximate to the living cell(s)/tissue 199 and/or to slide 200; but without transmitter 119 and pickup/receiver 147 adversely interfering with each other.

Figure 4:
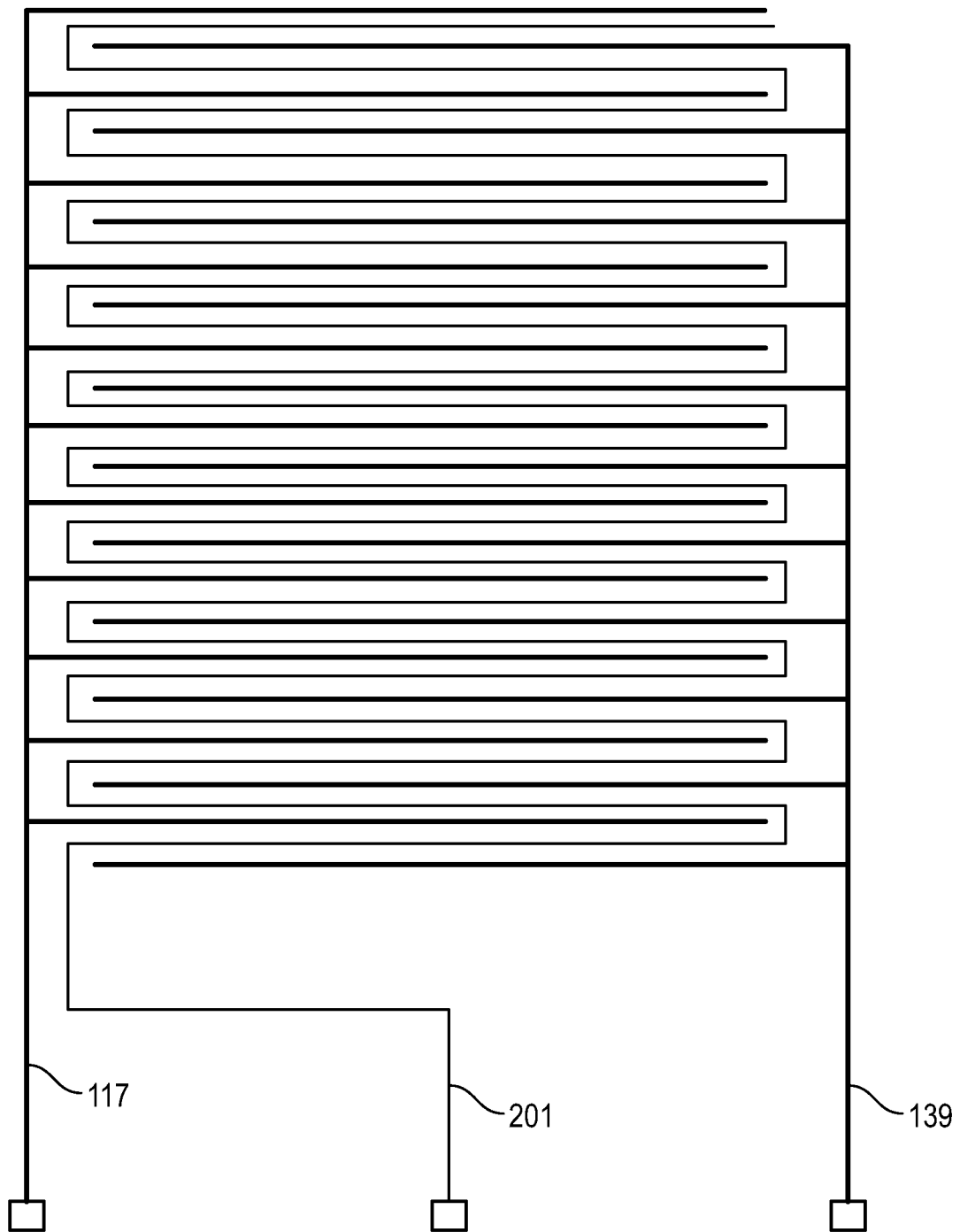
FIG. 4 may depict details of a conductive trace/electrode pattern that may be applied to a microscope slide.

FIG. 4 may depict details of a conductive trace/electrode pattern that may be applied to a surface of a given microscope slide 200. FIG. 4 may show one possible trace detail per some embodiments that may be rendered on a substantially optically clear conductive film which may be applied to a glass, polycarbonate, or the like microscope slide 200. In some embodiments, the clear conductive film may comprise conductive traces/electrodes 117, 139, and/or 201 that may be printed (attached to) upon a surface of slide 200. In some embodiments, the conductive traces/electrodes 117, 139, and/or 201 may be separated by conductive neutralized areas between the conductive traces/electrodes. In some embodiments, each conductive trace/electrode on a surface of slide 200 may be distinct and not in physical contact with another such conductive trace/electrode on a surface of slide 200. In some embodiments, distances between distinct conductive trace/electrode on a surface of slide 200 may be predetermined. In some embodiments, distances between distinct conductive trace/electrode on a surface of slide 200 may be fixed. In some embodiments, a top surface of slide 200 may comprise at least two traces/electrodes (e.g., input conductive trace 117 and output conductive trace 139). In some embodiments, a top surface of slide 200 may comprise at least three traces/electrodes of: input conductive trace 117, output conductive trace 139, and conductive trace/electrode 201. In some embodiments, conductive trace/electrode 201 may function as a ground. In some embodiments, a given conductive trace/electrode of a surface of slide 200 may be configured to provide the electromagnetic energy of the particular characteristics (e.g., waveform 157) to the living cell(s)/tissue 199. In some embodiments, a given conductive trace/electrode of a surface of slide 200 may be configured to receive the electromagnetic energy of a particular characteristic from the living cell(s)/tissue 199.

Continuing discussing electro medical tool 100, in some embodiments, a user of electro medical tool 100 may initially set frequency/waveform generator 101 to sweep outputs from DC up to the frequency limits of frequency/waveform generator 101 at a particular sweep rate not to exceed the image and data acquisition limits of camera 129. In some embodiments, software 151 may initially set frequency/waveform generator 101 to sweep outputs from DC up to the frequency limits of frequency/waveform generator 101 at a particular sweep rate not to exceed the image and data acquisition limits of camera 129. In some embodiments, when cellular behavior alteration 155 occurs, the frequency/waveform generator 101 waveform 157 being output at that moment may be locked in by a user or software 151 and the signal amplitude may be raised or lowered or the pulse width or duty cycle may be altered and living cell(s)/tissue 199 monitored for any further changes. Frequency/waveform generator 101 may then be directed by a user or software 151 to add a harmonic 159 of root waveform 157 to waveform 157 and living cell(s)/tissue 199 monitored for any further changes. Additional harmonics from 159$i$ to 159$n$, as well as wave shape, and amplitude alterations may also be tested until no more cellular behavior alteration 155 occurs. See e.g., FIG. 1.

Continuing discussing electro medical tool 100, in some embodiments, a user of electro medical tool 100 may also manually choose to lock-in or sweep through the light wavelength 111 outputs of monochromator 109 and/or of variable color source 113 colors 115. In some embodiments, software 151 may also be configured to sweep through and lock in any wavelength 111 or colors 115 of light, or combinations of the light outputs of monochromator 109 and variable color source 113 at a particular sweep rate not to exceed the image and data acquisition limits of camera 129. See e.g., FIG. 1.

Those frequency waves that are most absorbed by living cell(s)/tissue 199 may be considered for the purposes of the at least some embodiments, "resonant frequencies" of living cell(s)/tissue 199. In some embodiments, these "resonant frequencies" may be a subset of any available waveform 157 and must initially be identified through use of electro medical tool 100 (or sensor tool 900), and are then integrated within database 137 as lookup tables. "Overdriving" the amplitude of said resonant frequencies with respect to a base rate of frequency absorption of living cell(s)/tissue 199, said rate data contained in database 137, may affect the electrical conductivity and the chemical and mechanical conditions of living cell(s)/tissue 199. These resonant frequencies may then be manipulated and augmented by changes in pulse rate, amplitude, and wave shape, as well as the addition of frequency inversions, harmonics, and dissonances of said resonant frequencies by software 151 through computer 133 and frequency/waveform generator 101 and living cell(s)/tissue 199 monitored for any further changes. In some embodiments, manipulation of these resonant frequencies, combined with other waveforms 157 and one or more of harmonics 159 through 159$n$ may induce/catalyze a particular cellular behavior alteration 155; which may be monitored and documented (e.g., in database 137).

Such resonant frequencies, combined with other waveforms 157 and/or harmonic 159 through 159$n$, may be applied to induce/catalyze a particular cellular behavior/outcome (good or bad)—initially by altering a single specific structure or behavior within a cell of living cell(s)/tissue 199, and then outputting and altering additional applied waveforms 157 and/or harmonic 159 through 159$n$ combinations, which may then propagate state changes in other cell structures and mechanics like a domino effect for a more complete cellular response, outcome, and/or behavior.

Figure 5:
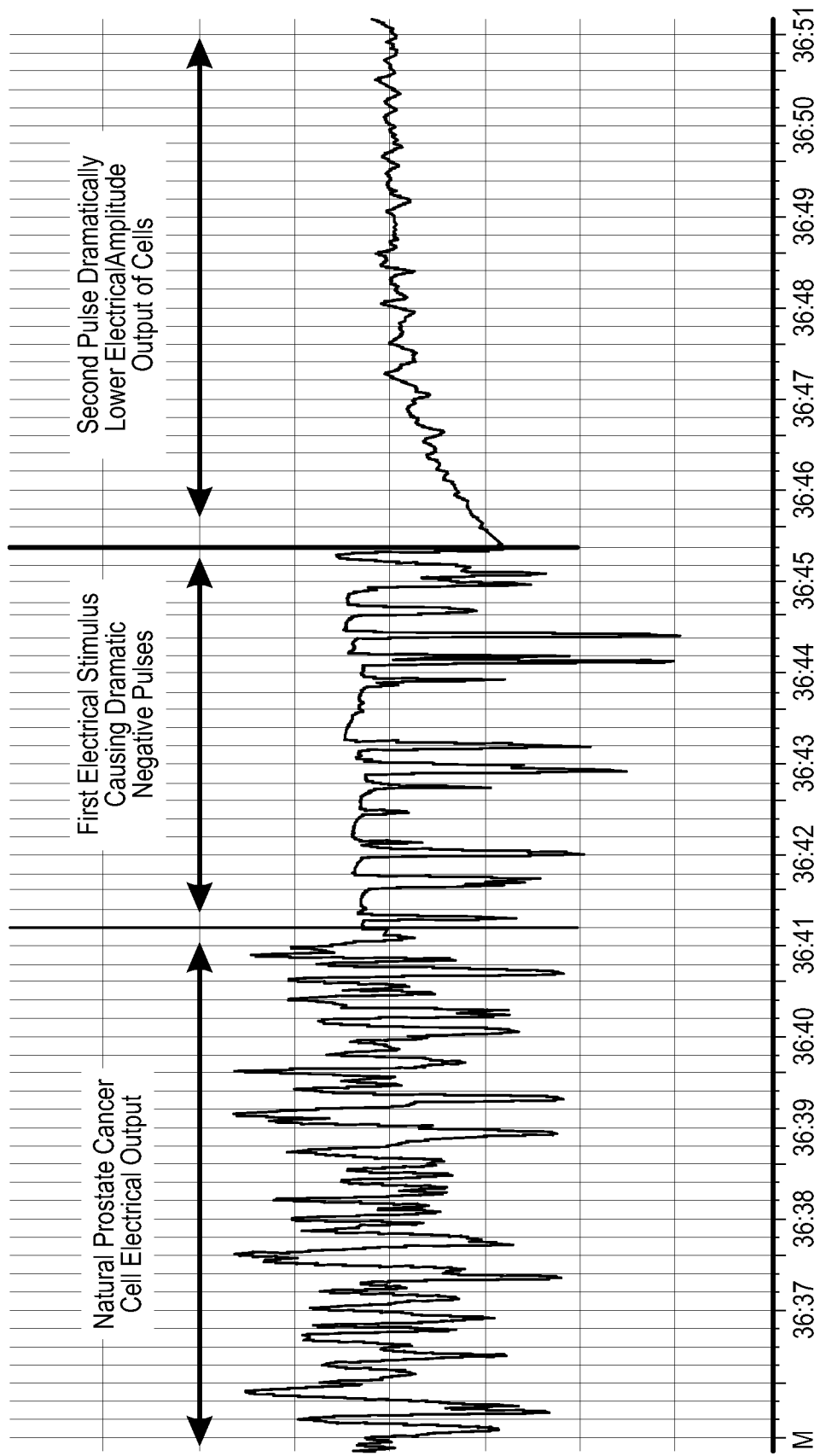
FIG. 5 may depict, as an example, an electroencephalogram (EEG) of healthy prostate cancer cells over time, showing the normal and/or the natural electrical fingerprint (e.g., EEG) of these healthy prostate cancer cells first without any electrical stimulus and then exposed to a first pulse and then exposed to a second pulse.

FIG. 5 may depict, as an example, an electroencephalogram (EEG) of healthy prostate cancer cells over time, from no pulse (left side), to a first pulse (middle), and to a second pulse (right side). FIG. 5 may have been generated from use of electro medical tool 100, with living cell(s)/tissue 199 being healthy prostate cancer cells. The horizontal axis may be time (minutes and seconds). The vertical axis may be amplitude in portions of a plus (+) or a minus (−) five (5) volt increment range. A left most region (labeled as, "Natural Prostate Cancer Cell Electrical Output") may show the normal and/or natural electrical fingerprint of these healthy prostate cancer cells without any electrical stimulus. A first bioactive pulse output (shown in the middle region and labeled as, "First Electrical Stimulus Causing Dramatic Negative Pulses") renders the amplitude output/response from these healthy prostate cancer cells into negative only pulses of zero (0) to minus five (−5) volts. And a second pulse output/response (shown in the righthand region and labeled as, "Second Pulse Dramatically Lower Electrical Amplitude Output of Cells") lowers the entire amplitude from these prostate cancer cells so that only a few pulses are a fraction of a plus volt and most pulses are a fraction of a negative volt. Based on such use of electro medical tool 100, it has been found that each different type of cell has its own natural/normal electrical fingerprint (e.g., EEG).

Figure 9:
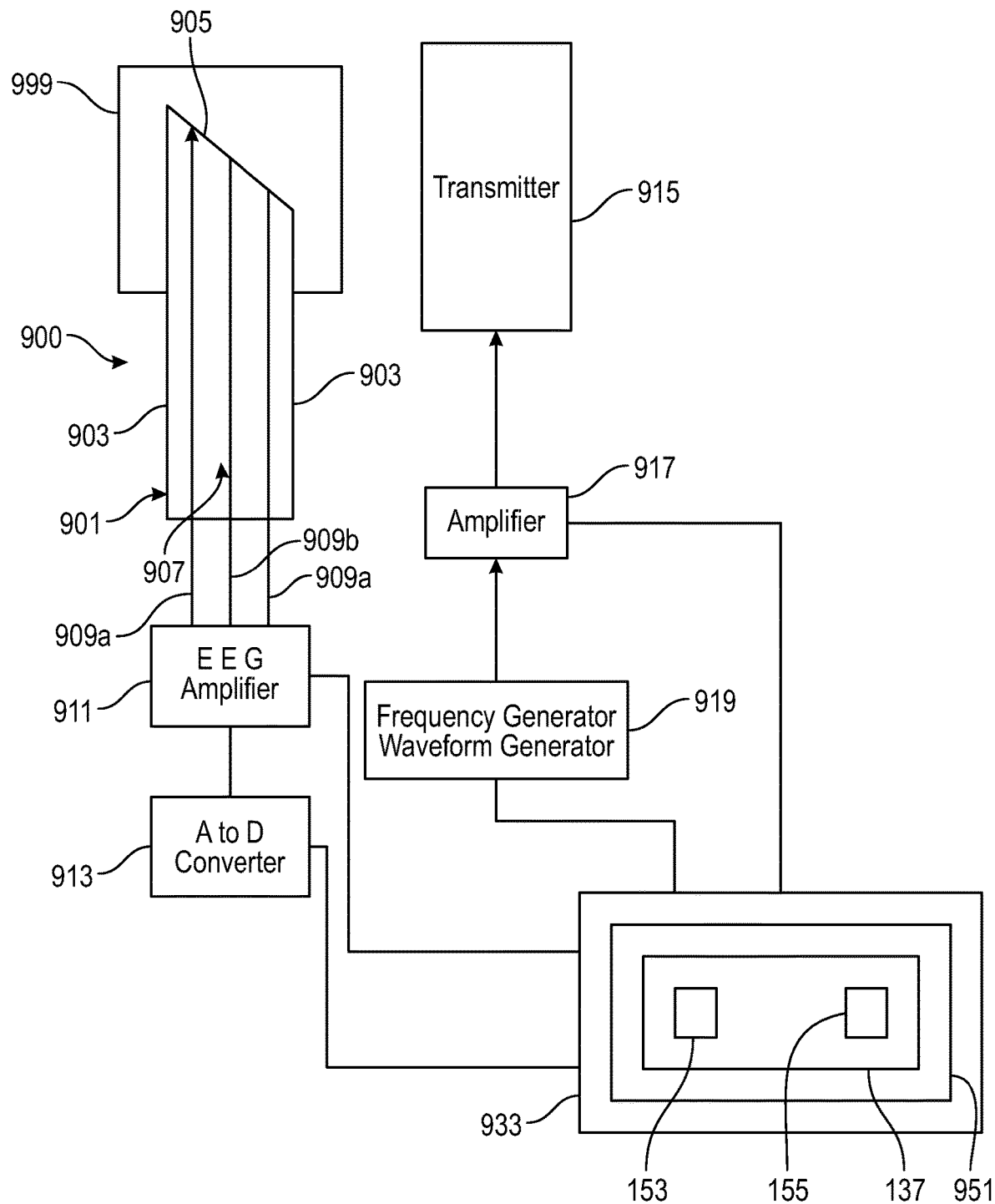
FIG. 9 may be a schematic block diagram illustrating a mildly invasive in vivo electro medical sensor tool used to determine bioactive electromagnetic frequencies and associated characteristics for a given and/or predetermined type of cell(s) and/or tissue.

Note, FIG. 5 or its equivalents could also be generated by using sensor tool 900 (with electro medical tool 100 [e.g., with sensor tool 900 electrodes replacing electrodes of electro medical tool 100] and/or with treatment tool 1000). (Sensor tool 900 and treatment tool 1000 are discussed below and are shown in FIG. 9 and in FIG. 10, respectively.)

Figure 6:
FIG. 6 may depict an example of a microscopy image of healthy prostate cancer cells before exposure to electromagnetic energy of a predetermined characteristic.

FIG. 6 may depict an example of a microscopy image of healthy prostate cancer cells before exposure to electromagnetic energy of a predetermined characteristic. FIG. 6 may have been generated from use of electro medical tool 100, with living cell(s)/tissue 199 being healthy prostate cancer cells.

Figure 7:
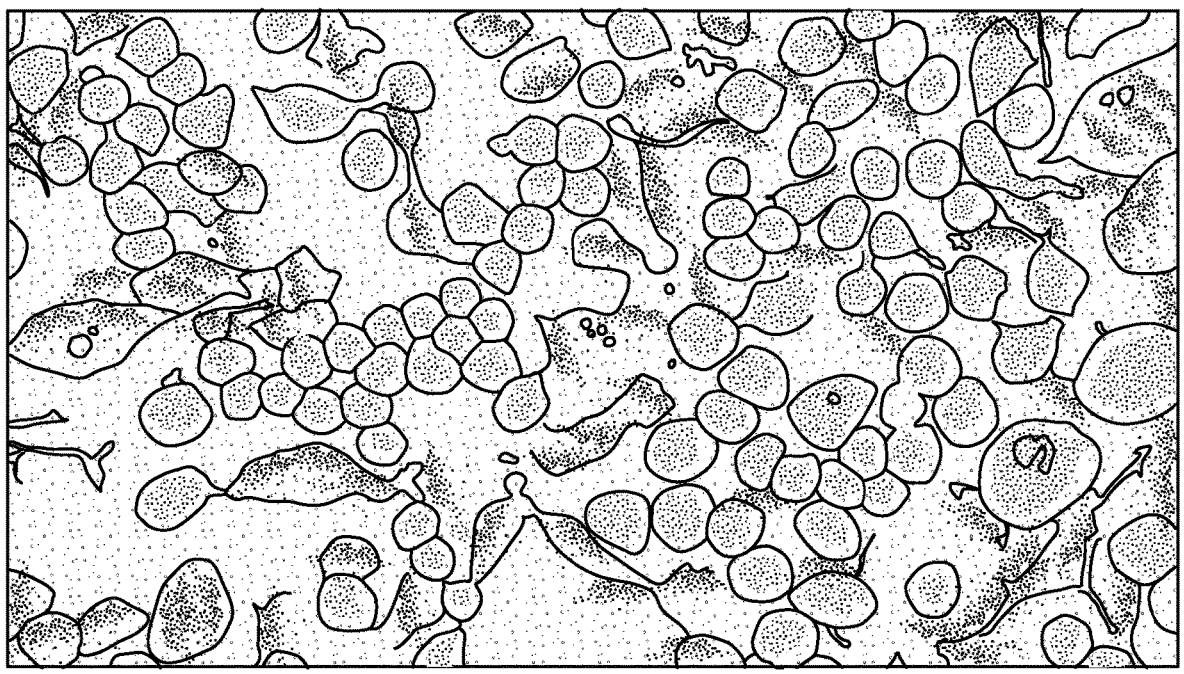
FIG. 7 may depict an example of a microscopy image of the formerly healthy prostate cancer cells after exposure to the electromagnetic energy of the predetermined characteristic, showing these prostate cancer cells destroyed, dying, and dead.

FIG. 7 may depict an example of a microscopy image of the formerly healthy prostate cancer cells, initially shown in FIG. 6, but now in FIG. 7 after exposure to the electromagnetic energy of the predetermined characteristic, showing at least a majority of these exposed prostate cancer cells dead and dying as a result of the exposure. FIG. 7 frequencies and waveforms may have been generated from use of electro medical tool 100, with living cell(s)/tissue 199 being the initially healthy prostate cancer cells. The electromagnetic energy of the predetermined characteristic used to generate the dying prostate cancer cells shown in FIG. 7 may have been one or more of: a 2 kilohertz (kHz) square wave at six minutes duration; a 4 kHz square wave at six minutes duration; a 14 kHz sine wave at six minutes duration; and/or a 20 kHz sine wave at six minutes duration. In some embodiments, the treatment tool 1000 may be configured to generate/output such electromagnetic energy of these predetermined characteristics (see e.g., FIG. 10 and its discussion).

Figure 8:
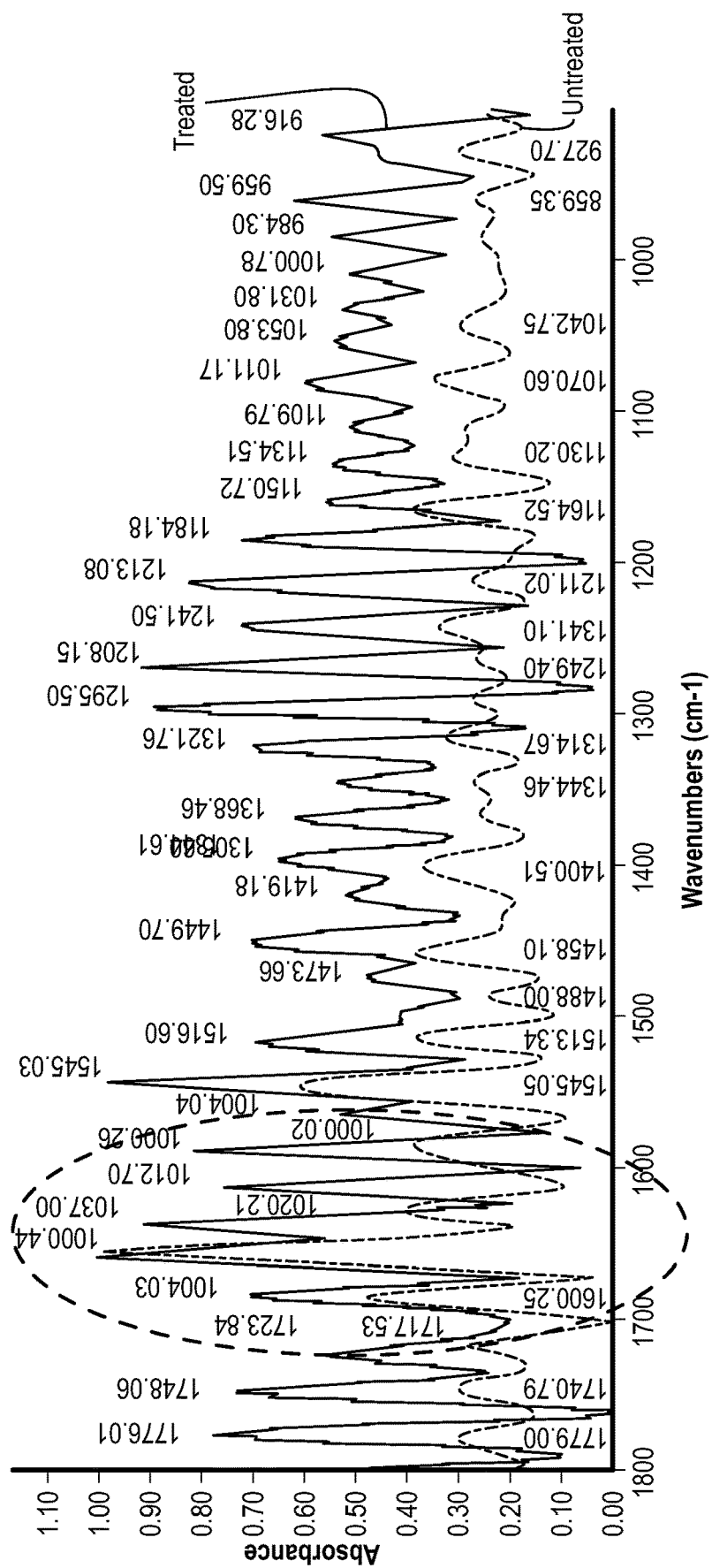
FIG. 8 may depict a broadband infrared spectrograph of cancerous prostate cells pre and post exposure to a predetermined range of electromagnetic energy and associated characteristics; and showing a shift in wavenumbers arising from the exposure of the predetermined range of electromagnetic energy and associated characteristics.

FIG. 8 may depict an example broadband infrared spectrograph of cancerous prostate cells pre and post exposure to a predetermined range of electromagnetic energy and associated characteristics (e.g., waveform 157) generated from use of electro medical tool 100. The vertical axis may be of absorbance amplitude and the horizontal axis is of wavenumbers (e.g., cm-1). More specifically, FIG. 8 may an example spectrograph derived from broadband infrared power amplifier data acquisition (such as, but not limited to, Fourier Transform Infrared Spectroscopy [FTIR]). In some embodiments, the FIG. 8 infrared data pre and post exposure, may show wavenumber shifts in protein zones (e.g., protein amide bands around 1900 to 1700 wavenumbers) and/or in membrane lipids (e.g., 1100 to 1400 wavenumbers), wherein this wavenumber shift may demonstrate protein misfolding and/or cell membrane increased permeability. Protein misfolding may alert the immune system to a cell type that should be targeted for destruction, destroying the cell with the misfolded proteins, and/or to the existence of cancer. Selective increased membrane permeability provides a route for better use of chemotherapy by better selectivity, reduced dosage, and increased cancer cell kill rate.

Note, the electromagnetic energy of the predetermined characteristics used to expose the cells of FIG. 8 may have been generated using electro medical tool 100, but treatment tool 1000 could also have generated this electromagnetic energy of the predetermined characteristics.

FIG. 9 may be a schematic block diagram illustrating a mildly invasive electro medical sensor tool 900 used to determine bioactive electromagnetic frequencies and associated characteristics for a given and/or predetermined type of cell(s) and/or tissue, designated as region of tissue 999. In some embodiments, sensor tool 900 may be used for a substantially same purpose as 100, i.e., to determine bioactive electromagnetic frequencies and associated characteristics for a given and/or predetermined type of cell(s) and/or tissue. In some embodiments, sensor tool 900 may differ from electro medical tool 100, in that sensor tool 900 may be used in an in vivo manner; whereas, electro medical tool 100 may largely be used in an in vitro manner. In some embodiments, sensor tool 900 may be mildly invasive. In some embodiments, sensor tool 900 may comprise a needle 901, wherein needle 901 may be configured to be inserted into region of tissue 999 of a given living organism. In some embodiments, the given living organism may be any living species (such as, but not limited to, humans), a hybrid species, a manufactured species, portions thereof, combinations thereof, and/or the like.

Continuing discussing FIG. 9, in some embodiments, sensor tool 900 may comprise at least one needle 901, at least two or more leads/electrodes, at least one amplifier 911 (such as, but limited to, an EEG type of amplifier), and at least one A to D converter 913.

Continuing discussing FIG. 9, in some embodiments, needle 901 may be substantially cylindrical with sidewalls 903. In some embodiments, sidewalls 903 may house one or more leads/electrodes of sensor tool 900. In some embodiments, needle 901 may comprise a distal/terminal end configured for piercing into skin, flesh, tissue, and/or region of tissue 999. In some embodiments, that distal/terminal end of needle 901 may be designated tip/opening 905. In some embodiments, tip/opening 905 may be a terminal/distal portion of needle 901 (e.g., disposed away from amplifier 911). In some embodiments, tip/opening 905 may have one or more opening(s) configured for permitting physical contact with leads/electrodes of sensor tool 900 with region of tissue 999. In some embodiments, sidewalls 903 may transition into tip/opening 905. In some embodiments, needle 901 may comprise at least one lumen 907. In some embodiments, needle 901 may comprise one or more lumens 907. In some embodiments, needle 901 may comprise one lumen 907 per each lead/electrode of sensor 900. In some embodiments, an exterior of needle 901, sidewalls 903, tip 905, and/or lumen(s) 907, may be substantially constructed from one or more stainless steels or non conductive lead guides. In some embodiments, sidewalls 903 may be marked/graduated at predetermined and fixed distances/lengths along needle 901, in order to facilitate determination of how far needle 901 might be inserted into region of tissue 999. In some embodiments, such markings/graduations may extend from tip 905. In some embodiments, a lumen 907 of needle 901 may comprise at least one surgical (fiberoptic) microscope.

Continuing discussing FIG. 9, in some embodiments, the leads/electrodes of sensor tool 900 may be designated lead/electrode 909. In some embodiments, a given lead/electrode 909 may be an elongate member. In some embodiments, a given lead/electrode 909 may be substantially electrically conductive. In some embodiments, a central elongate core of a given lead/electrode 909 may be substantially electrically conductive. In some embodiments, substantially/mostly all of the electrically conductive portions of a given lead/electrode 909 may be substantially/mostly made of copper. In some embodiments, a distal/terminal portion of a given lead/electrode 909 may be substantially/mostly made of gold. In some embodiments, a distal/terminal portion of a given lead/electrode 909 may be gold tipped. In some embodiments, a given lead/electrode 909 may comprise substantially non-electrically conductive regions that may electrically insulate at least portions of the given lead/electrode 909. (The lumen does this) In some embodiments, a given lead/electrode 909 may be a wire configured to communicate electricity. In some embodiments, sensor tool 900 may comprise at least one hot lead 909a and at least one ground 909b. In some embodiments, leads/electrodes 909 may comprise at least one hot lead 909a and at least one ground 909b. In some embodiments, sensor tool 900 may comprise at least two hot leads 909a and at least one ground 909b. In some embodiments, leads/electrodes 909 may comprise at least two hots lead 909a and at least one ground 909b. In some embodiments, leads/electrodes 909 may be operatively connected to amplifier 911. See e.g., FIG. 9.

Continuing discussing FIG. 9, in some embodiments, amplifier 911 may amplify outputs from A to D converter 913. In some embodiments, amplifier 911 may be operatively connected to A to D converter 913. In some embodiments, amplifier 911 may be operatively connected to leads/electrodes 909. In some embodiments, amplifier 911 may be substantially configured as an EEG (electroencephalography) amplifier. See e.g., FIG. 9.

Continuing discussing FIG. 9, in some embodiments, A to D converter 913 may convert analog inputs to digital outputs. In some embodiments, digital outputs of 913 may be communicated to a computer 933 for non-transitory storage in database 137. In some embodiments, computer 933 may be operatively connected to amplifier 911 and/or to A to D converter 913, in a same manner that computer 133 may be operatively connected to components of electro medical tool 100.

Continuing discussing FIG. 9, in some embodiments, sensor tool 900 may also utilize at least one transmitter 915, at least one amplifier 917, and at least one frequency/waveform generator 919. In some embodiments, transmitter 915 may be operatively connected to amplifier 917. In some embodiments, amplifier 917 may be operatively connected to frequency/waveform generator 919. In some embodiments, transmitter 915 may be operatively connected to frequency/waveform generator 919.

Continuing discussing FIG. 9, in some embodiments, transmitter 915 may be substantially similar to transmitter 119 (e.g., in terms of purpose and/or in terms of architecture). In use, transmitter 915 may be placed/located proximate to region of tissue 999 and/or to needle 901 within region of tissue 999. In some embodiments, transmitter 915 may be configured to transmit/broadcast/emit a waveform 157 output from frequency/waveform generator 919 directed to/towards region of tissue 999. In some embodiments, transmitter 915 may be a single transmitter or a plurality of transmitters. In some embodiments, transmitter 915 may be one or more of an antenna, a transducer, a coil, portions thereof, combinations thereof, and/or the like. In some embodiments, transmitter 915 may have a frequency response at least equal to an output from frequency/waveform generator 919 (e.g., waveform 157). In some embodiments, transmitter 915 may be replaceable, swappable, and/or equivalent to transmitter 119.

Continuing discussing FIG. 9, in some embodiments, amplifier 917 may be substantially similar to amplifier 105 (e.g., in terms of purpose and/or in terms of architecture). In some embodiments, amplifier 917 may have a frequency response at least equal to an output from frequency/waveform generator 919 (e.g., waveform 157). In some embodiments, amplifier 917 may be replaceable, swappable, and/or equivalent to amplifier 105.

Continuing discussing FIG. 9, in some embodiments, frequency/waveform generator 919 may be substantially similar to frequency/waveform generator 101 (e.g., in terms of purpose and/or in terms of architecture). In some embodiments, frequency/waveform generator 919 may output a given waveform 157. In some embodiments, frequency/waveform generator 919 may be replaceable, swappable, and/or equivalent to frequency/waveform generator 101.

Continuing discussing FIG. 9, in some embodiments, computer 933 may be substantially similar to computer 133 (e.g., in terms of purpose and/or in terms of architecture). In some embodiments, computer 933 may be operatively connected to amplifier 911, A to D converter 913, amplifier 917, frequency/waveform generator 919, portions thereof, combinations thereof, and/or the like. In some embodiments, computer 933 may comprise at least one screen/video display (such as, but not limited to, display 131) (e.g., for viewing data in database 137). In some embodiments, computer 933 may comprise one or more storage devices, such as, but not limited to hard drives or the like configured for the non-transitory storage of software 951, database 137, baseline cellular information 153, changed/deviated cellular information 155, portions thereof, combinations thereof, and/or the like. In some embodiments, computer 933 may be replaceable, swappable, and/or equivalent to computer 133. In some embodiments, software 951 may be substantially similar to software 151 (e.g., in terms of purpose and/or in terms of architecture). In some embodiments, software 951 may be replaceable, swappable, and/or equivalent to software 151.

In some embodiments, needle 901, and its electrodes 909, may be used in electro medical tool 100, by replacing electrodes of electro medical tool 100 (e.g., output conductive trace/electrode 139, input conductive trace/electrode 117, and/or conductive trace/electrode 201).

In some embodiments, sensor tool 900 may be used together with 1000 (described and discussed below) or portion thereof (e.g., transmitter 1001) for deriving and/or determining bioactive frequencies and/or associated characteristics (e.g., waveform 157) of a particular region of tissue 999.

Figure 10:
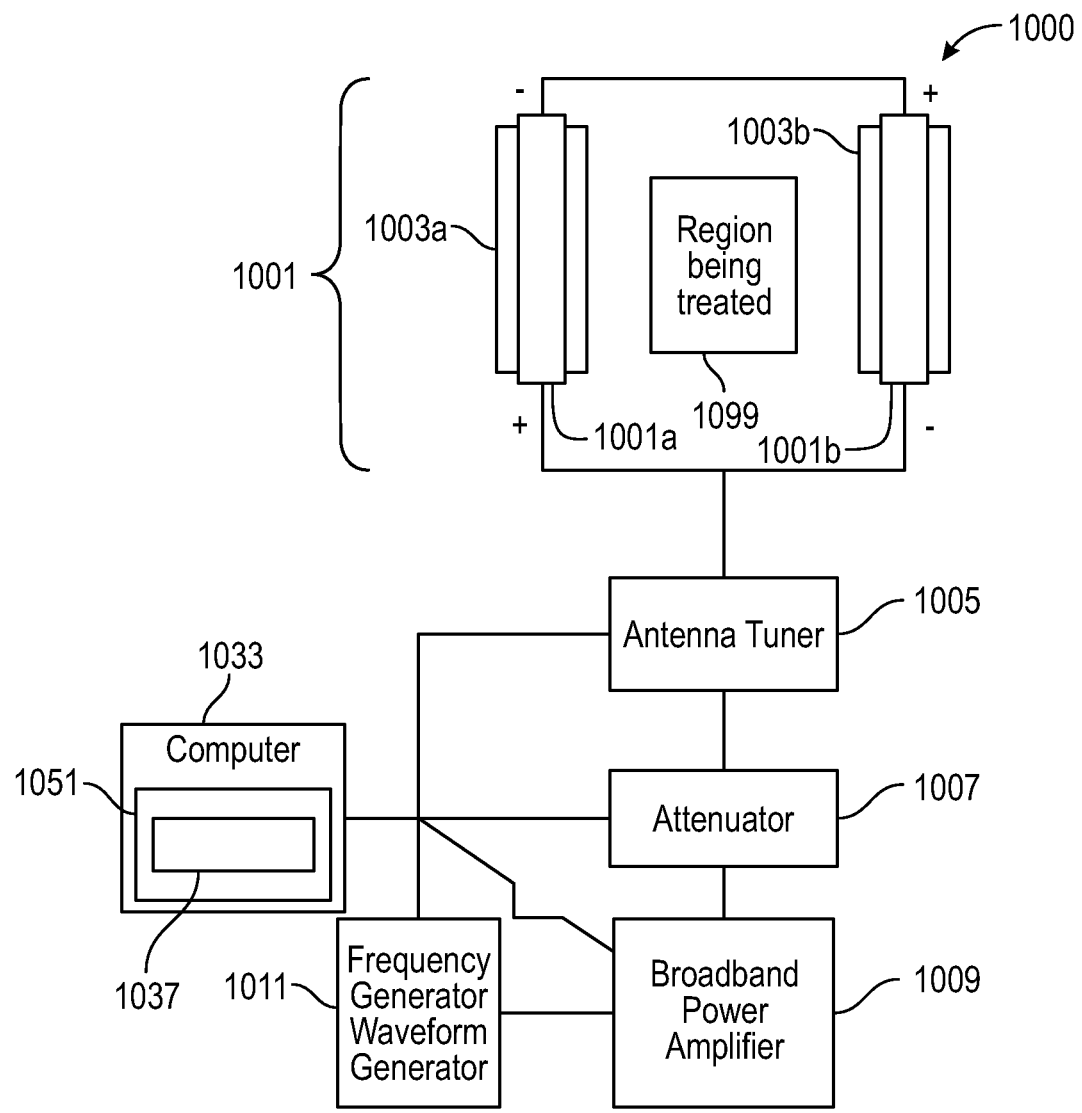
FIG. 10 may be a schematic block diagram illustrating an electro medical treatment tool used to apply predetermined bioactive electromagnetic frequencies and associated/or characteristics to a given and/or predetermined type of cell(s) and/or tissue for a particular outcome (and the treatment tool of FIG. 10 [or portion thereof] may be used in conjunction with the sensor tool [or portion thereof] of FIG. 9 to determine bioactive signals).

FIG. 10 may be a schematic block diagram illustrating an electro medical tool 1000, a treatment tool 1000, used to apply/direct/transmit predetermined bioactive electromagnetic frequencies and associated/or characteristics (e.g., waveform 157) to a given and/or to a predetermined type of at least one cell(s) 1099 and/or to a given and/or to a predetermined type of at least one tissue 1099 for a particular outcome. The electromagnetic characteristics that may be generated, broadcast, transmitted, varied, controlled, and applied from treatment tool 1000 to region being treated 1099 may comprise: frequency (or wavelength) (selected from the entire electromagnetic spectrum and/or from the acoustic spectrum); waveform (e.g., DC, sine, square, sawtooth, rising, falling, inversions, etc.); harmonic(s) of a given waveform; energy level applied; duration of exposure; portions thereof; combinations thereof; and/or the like.

Continuing discussing FIG. 10, in some embodiments, the bioactive electromagnetic frequencies and associated/or characteristics (e.g., waveform 157) outputted from treatment tool 1000 may be directed at and/or received in part at region being treated 1099. In some embodiments, region being treated 1099 may comprise at least one living cell, of a predetermined cell type, that is being specifically targeted by the output(s) of treatment tool 1000. In some embodiments, region being treated 1099 may also comprise one or more living cells of different type(s) that are not specifically being targeted by treatment tool 1000. In some embodiments, region being treated 1099 may comprise at least one living cell of a particular type that is being targeted by treatment tool 1000 and cell(s) of other different type(s) that are not being targeted by treatment tool 1000, but may still be exposed to output(s) of treatment tool 1000. In some embodiments, region being treated 1099 may comprise the entirety of at least one living organism, whether multicell or single celled. In some embodiments, region being treated 1099 may comprise at least one living organism, such as, but not limited to: a human, an animal, a vertebrate animal, a mammal, a primate, a plant, an algae, a fungus, a yeast, a protozoan, a eukaryotic organism, a prokaryotic organism, a bacteria, an archaebacteria, a hybrid organism, a chimera organism, or the like. In some embodiments, the cell(s) of region being treated 1099 may be in an in vivo setting. In some embodiments, at least most of the cell(s) of region being treated 1099 may be alive and/or living, at least before exposure from treatment tool 1000.

Continuing discussing FIG. 10, in some embodiments, a transmitter assembly 1001 of treatment tool 1000 may be a portion of treatment tool 1000 that outputs the predetermined bioactive electromagnetic frequencies and associated/or characteristics (e.g., waveform 157) to region being treated 1099. In some embodiments, region being treated 1099 may be disposed between different transmitter/receiver elements of transmitter assembly 1001. In some embodiments, transmitter assembly 1001 may be sized to fit a size of the region being treated 1099 between its transmitters/receivers. For example, and without limiting the scope of the present invention, when region being treated 1099 may be an entire human (e.g., when cancer may be widespread throughout the human), transmitter assembly 1001 may be sized comparably larger than when region being treated 1099 may be a region of skin on a single hand of the human (e.g., treating a single mole), in which case the given transmitter assembly 1001 may be sized comparably smaller. In some embodiments, transmitter assembly 1001 may transmit the outputted predetermined bioactive electromagnetic frequencies and associated/or characteristics (e.g., waveform 157) wirelessly to region being treated 1099. In some embodiments, coils (e.g., coil 1001a and coil 1001b) of transmitter assembly 1001 may be placed concentrically disposed around region being treated 1099, so that the outputted electromagnetic field (i.e., the outputted predetermined bioactive electromagnetic frequencies and associated/or characteristics [e.g., waveform 157]) passes directly through region being treated 1099. In some embodiments, transmitter assembly 1001 may transmit the outputted predetermined bioactive electromagnetic frequencies and associated/or characteristics (e.g., waveform 157) to region being treated 1099 without transmitter assembly 1001 physically touching region being treated 1099. In some embodiments, treatment tool 1000 may function non-invasively with respect to region being treated 1099. In some embodiments, transmitter assembly 1001 may transmit the outputted predetermined bioactive electromagnetic frequencies and associated/or characteristics (e.g., waveform 157) to region being treated 1099 with transmitter assembly 1001 physically touching region being treated 1099.

Continuing discussing FIG. 10, in some embodiments, a given electro medical tool 1000 may comprise at least one transmitter assembly 1001, at least one antenna tuner 1005, at least one attenuator 1007, at least one broadband power amplifier 1009, and at least one frequency/waveform generator 1011. In some embodiments, transmitter assembly 1001 may be operatively connected (wired) to antenna tuner 1005. In some embodiments, antenna tuner 1005 may comprise one or more of: a variable inductor and/or a variable capacitor. In some embodiments, antenna tuner 1005 may be operatively connected (wired) to attenuator 1007. In some embodiments, attenuator 1007 and antenna tuner 1005 together may be used to match impedances. In some embodiments, attenuator 1007 may be used to match impedances. In some embodiments, attenuator 1007 may have predetermined characteristics. In some embodiments, attenuator 1007 may be a one (1) decibel (dB) 50 ohm device. In some embodiments, attenuator 1007 may be a one (1) dB 300 watt 50 ohm attenuator. In some embodiments, attenuator 1007 may have other predetermined characteristics. In some embodiments, a combination of antenna tuner 1005 and the attenuator 1007 may provide an impedance matching effect. Without antenna tuner 1005 and attenuator 1007 (or their equivalents), transmitter assembly 1001 (e.g., coils 1001a and 1001b) may not be impedance matched; and in some embodiments, such an impedance mismatch may cause an unacceptable power mismatch with amplifier 1009. In electronic terms, the impedance match (via use of antenna tuner 1005 and attenuator 1007 [or their equivalents]) reduces the voltage standing wave ratio (VSWR) amplitude of the system. In some embodiments, attenuator 1007 may be operatively connected (wired) to broadband power amplifier 1009. In some embodiments, broadband power amplifier 1009 may have predetermined characteristics. In some embodiments, broadband power amplifier 1009 may be 100 watt (W) at 2 kilohertz KHZ to 100 megahertz (MHZ) broadband power amplifier. In some embodiments, broadband power amplifier 1009 may have other predetermined characteristics. In some embodiments, a power wattage of broadband power amplifier 1009 may be sized according to size, mass, and/or density of region being treated 1099. For example, and without limiting the scope of the present invention, when region being treated 1099 may be an entire human being, then wattage of broadband power amplifier 1009 may larger than when region being treated 1099 may be smaller. In some embodiments, broadband power amplifier 1009 may be operatively connected (wired) to frequency/waveform generator 1011. In some embodiments, frequency/waveform generator 1011 drives broadband power amplifier 1009. In some embodiments, frequency/waveform generator 1011 may be operatively connected (wired) to one or more power sources.

Continuing discussing FIG. 10, in some embodiments, frequency/waveform generator 1011 may generate at least one bioactive electromagnetic frequency and associated/or characteristics (e.g., waveform 157); while broadband power amplifier 1009, attenuator 1007, and antenna tuner 1005 may ensure and communicate the generated at least one bioactive electromagnetic frequency and associated/or characteristics (e.g., waveform 157) for output at transmitter assembly 1001 (e.g., through the treatment coils 1001a and 1001b). In some embodiments, the generated at least one bioactive electromagnetic frequency and associated/or characteristics (e.g., waveform 157) by frequency/waveform generator 1011 may be targeting a particular cell type of region being treated 1099 for inducing a particular outcome/behavior in that particular cell type of region being treated 1099. In some embodiments, the generated at least one bioactive electromagnetic frequency and associated/or characteristics (e.g., waveform 157) by frequency/waveform generator 1011 may have been determined from use of electro medical tool 100 and/or sensor tool 900.

Continuing discussing FIG. 10, in some embodiments, a given transmitter assembly 1001 may be configured for wireless transmission of the generated at least one bioactive electromagnetic frequency and associated/or characteristics (e.g., waveform 157). In some embodiments, a given transmitter assembly 1001 may be configured as an antenna, a transducer, a transmitter, a receiver, a Helmholtz pair of coils, portions thereof, combinations thereof, and/or the like. In some embodiments, a given transmitter assembly 1001 may comprise a pair of spaced coils (e.g., coil 1001a and 1001b). In some embodiments, each coil may be of a predetermined: conductive material, gauge/diameter, length, number of turns, turn spacing, insulation, portions thereof, combinations thereof, and/or the like. For example, and without limiting the scope of the present invention, coil 1001a and/or 1001b may be sixteen (16) gauge insulated cooper wire, multi-thread, with seven (7) turns. In other embodiments, other coil characteristics may be used. In some embodiments, each coil may be wound around a substantially non-electrically conductive bobbin 1003. In some embodiments, bobbin 1003 may comprise bobbin 1003a and bobbin 1003b. In some embodiments, bobbin 1003 may be at least substantially constructed from at least one non-electrically conductive plastics. In some embodiments, coil 1001a may be wound around bobbin 1003a. In some embodiments, coil 1001b may be wound around bobbin 1003b. In some embodiments, coil 1001a and coil 1001b may be wired in series. In some embodiments, coil 1001a and coil 1001b may form a Helmholtz pair of coils. In some embodiments, polarity of coil 1001a and coil 1001b may be shown in FIG. 10 by plus and minus symbols.

Continuing discussing FIG. 10, in some embodiments, a computer 1033 may be operatively linked to (wired to) one or more of: transmitter assembly 1001, coil 1001a, coil 1001*b*, antenna tuner 1005, attenuator 1007, broadband power amplifier 1009, frequency/waveform generator 1011, portions thereof, combinations thereof, and/or the like. In some embodiments, computer 1033 may control, instruct, sense, monitor, receive data from, transmit data to, receive feedback, transmit instructions, portions thereof, combinations thereof, and/or the like with respect to one or more of: transmitter assembly 1001, coil 1001*a*, coil 1001*b*, antenna tuner 1005, attenuator 1007, broadband power amplifier 1009, frequency/waveform generator 1011, portions thereof, combinations thereof, and/or the like. In some embodiments, computer 1033 may substantially similar to computer 133, computer 933, and/or the like. In some embodiments, computer 1033 may comprise one or more processors, memory (e.g., DRAM or the like), storage (e.g., hard-drive or the like), I/O means, network card/antenna, power source, portions thereof, and/or the like.

Continuing discussing FIG. 10, in some embodiments, software 1051 may be non-transitorily stored in storage of computer 1033. In some embodiments, software 1051 when in use may be called up into the memory of computer 1033 and interacted with via the one or more processors of computer 1033. In some embodiments, database 1037 may be non-transitorily stored in storage of computer 1033. In some embodiments, database 1037 may a plurality of predetermined bioactive electromagnetic frequencies and associated/or characteristics (e.g., waveform 157) associated with a given and/or a predetermined type of at least one cell(s) 1099 and/or associated with a given predetermined type of at least one tissue 1099; and wherein each of the predetermined bioactive electromagnetic frequencies and associated/or characteristics (e.g., waveform 157) may be associated with a particular outcome/induced cellular outcome/behavior. In some embodiments, database 1037 may be substantially similar to database 137. In some embodiments, database 1037 may be derived from database 137. In some embodiments, database 1037 may be a subset of database 137. In some embodiments, software 1051 may use a given predetermined bioactive electromagnetic frequencies and associated/or characteristics (e.g., waveform 157) selected from database 1037 for output at transmitter assembly 1001. In some embodiments, software 1051 may be configured to: control, instruct, sense, monitor, receive data from, transmit data to, receive feedback, transmit instructions, portions thereof, combinations thereof, and/or the like with respect to one or more of: transmitter assembly 1001, coil 1001*a*, coil 1001*b*, antenna tuner 1005, attenuator 1007, broadband power amplifier 1009, frequency/waveform generator 1011, portions thereof, combinations thereof, and/or the like.

Continuing discussing FIG. 10, in some embodiments, treatment tool 1000 may comprise transmitter assembly 1001, coil 1001*a*, coil 1001*b*, bobbin 1003*a*, bobbin 1003*b*, antenna tuner 1005, attenuator 1007, broadband power amplifier 1009, frequency/waveform generator 1011, computer 1033, portions thereof, combinations thereof, and/or the like.

In some embodiments, treatment tool 1000 may be used to apply/direct/transmit the given predetermined bioactive electromagnetic frequencies and associated/or characteristics (e.g., waveform 157) to a given and/or to a predetermined type of at least one targeted cell(s) type selected from region of treatment 1099 for a particular cellular outcome/behavior in at least one targeted cell(s) type. In some embodiments, the particular cellular outcome/behavior may be one or more of: cell cycle initiation (inducement of mitosis and/or meiosis); cell growth/expansion; cell collapse/shrinkage; cell movement (e.g., increase or decrease); cell cycle arrest (cessation of mitosis and/or meiosis); cell death (e.g., apoptosis and/or necrosis); changes in cell membrane permeability; increased cell membrane permeability; decreased cell membrane permeability; protein misfolding (partial protein denaturation); changes in cellular morphology; changes in cell wall (for a cell with a cell wall); portions thereof; combinations thereof; and/or the like.

In some embodiments, one or more of such induced cellular outcomes/behaviors may be used as at least part of a given treatment. In some embodiments, the treatment may be therapeutic, necessary, desired, cosmetic, elective, portions thereof, combinations thereof, and/or the like.

For example, and without limiting the scope of the present invention, treating to rid a given host of an undesirable cell type, using treatment tool 1000 to output predetermined bioactive electromagnetic frequencies and associated/or characteristics (e.g., waveform 157) transmitted to region being treated 1099, that contains the undesirable cell type and that may contain other different cell types (that may be desirable), may fall into five main methodologies: (a) exposing/dosing region being treated 1099 for inducing death in the treated undesirable cell; (b) exposing/dosing region being treated 1099 for inducing increased cellular permeability in the treated undesirable cell, which in turn may result in uptake of predetermined chemotherapy drug(s) into that treated undesirable cell for safer and more effective chemotherapy treatment; (c) exposing/dosing region being treated 1099 for inducing increased cellular permeability in the treated undesirable cell, which in turn may result in presentation of a predetermined marker/signal molecule, wherein that now marked undesirable cell may be made visible to the host's own immune system such that the host's own immune system may be able to identify and target that marked undesirable cell for destruction; (d) exposing/dosing region being treated 1099 for inducing protein misfolding of that undesirable cell, which in turn may result in the host's own immune system being able to identify and target that treated undesirable cell for destruction via the host's own immune system; (e) exposing/dosing region being treated 1099 for weakening/harming the undesired cell, which in turn may make the so treated undesired cell more vulnerable to otherwise traditional indiscriminate chemotherapy and/or to radiation therapy; portions thereof; combinations thereof; and/or the like; and any of the above noted undesirable cell treatments may be done in vivo, non-invasively, and/or without harming other different cells/tissue types of region being treated 1099.

In some embodiments, the undesirable cell may be selected from: a cancer cell, a tumor cell, a cell with a broken cell cycle, an infected cell, a viral infected cell, a bacteria infected cell, a protozoan infected cell, a foreign cell (e.g., a cell not from the host of region of treatment 1099), an abnormal cell, a scar tissue cell, a wrinkle cell, a fat cell, a skin cell, a gland cell, a nerve cell, a breast tissue cell, a hybrid cell, a chimeric cell, portions thereof, combinations thereof, and/or the like.

For example, and without limiting the scope of the present invention, if the host is a vertebrate animal of a particular species, then a foreign cell may be one or more of: a bacterial cell, a protozoan cell, a fungal cell, a plant or algae cell; a cell from a different species, a cell from the same species but from a different individual, portions thereof, combinations thereof, and/or the like. For example, and without limiting the scope of the present invention, an undesirable skin cell may be a skin cell that generates too much hair/keratin and/or hair/keratin with undesirable characteristics (e.g., too thick). For example, and without limiting the scope of the present invention, an undesirable gland cell may be a gland that may be producing/secreting/outputting too much of a given molecule (e.g., saliva, mucus, hormone, neurotransmitter, and/or the like). For example, and without limiting the scope of the present invention, an undesirable nerve cell may be generating chronic pain and/or stuck in a manner that generates constant to near constant pain.

For example, and without limiting the scope of the present invention, treatment tool 1000 may be used to treat various cancers, tumors, and/or cells with broken cell cycles that may be in a state of unregulated/controlled growth and/or cell division. For example, and without limiting the scope of the present invention, using treatment tool 1000, predetermined bioactive electromagnetic frequencies and associated/or characteristics (e.g., waveform 157) may be transmitted to region being treated 1099 for predetermined outcomes as follows: (a) a predetermined type of cancer cell may be targeted and exposed/dosed inducing death in that treated cancer cell; (b) a predetermined type of cancer cell may be targeted and exposed/dosed inducing increased cellular permeability in that treated cancer cell, which in turn may result in uptake of predetermined chemotherapy drug(s) into that treated cancer cell for safer and more effective chemotherapy treatment; (c) a predetermined type of cancer cell may be targeted and exposed/dosed inducing increased cellular permeability in that treated cancer cell, which in turn may result in the presentation of a predetermined marker/signal molecule, wherein that now marked cancer cell may be made visible to the host's own immune system such that the host's own immune system may be able to identify and target that marked cancer cell for destruction; (d) a predetermined type of cancer cell may be targeted and exposed/dosed inducing protein misfolding of that cancer cell, which in turn may result in the host's own immune system being able to identify and target that treated cancer cell for destruction via the host's own immune system; (e) a predetermined type of cancer cell may be targeted and exposed/dosed inducing weakening/harming (e.g., from induced protein misfolding) of the given cancer cell, which in turn may make the so treated cancer cell more vulnerable to otherwise traditional indiscriminate chemotherapy and/or to radiation therapy; portions thereof; combinations thereof; and/or the like; and any of the above noted cancer treatments may be done in vivo, non-invasively, mildly invasively, and/or without harming other different cells/tissue types of region being treated 1099.

| Cell Type | Bioactive Frequencies Characteristics | Effect(s) on Cell Type |
|---|---|---|
| Human Prostate Cancer (LCVMS Prostate Cancer Frequency Set 1)* | 450 hertz (Hz) square, 2008 Hz square, 4000 Hz ramp, 6022 Hz square, 14000 Hz sine, 20000 Hz sine; with durations from two to eight minutes | Destructive effects include cessation of mitosis, apoptosis, necrosis, increased cell membrane permeability, protein misfolding, and granulation of cellular mechanics. |
| Human Prostate Cancer (LCVMS Prostate Cancer Frequency Set 2)* | 450 Hz, 489 Hz, 583 Hz, 971.3 Hz, 4000 Hz, 6022 Hz, 7402 Hz, 10542 Hz, 11300 Hz; all square waveforms; with durations of eight minutes | Destructive effects include cessation of mitosis, apoptosis, necrosis, increased cell membrane permeability, protein misfolding, and granulation of cellular mechanics. |
| Human Prostate Cancer (LCVMS Cancer Frequency Set 3 [most derived from tracking generator absorption analysis])* | 317 kilohertz (kHz), 544 kHz, 947 kHz, 1.220 megahertz (MHz), 2.467 MHz, 4.812 MHz, 5.265455 MHz, 5.9 MHz, 11.300 MHz, 11.780 MHz, 17.045455 MHz, 28.823455 MHz; sine waves; 30 minutes (min.) each | Destructive effects include cessation of mitosis, apoptosis, necrosis, increased cell membrane permeability, protein misfolding, and granulation of cellular mechanics. |
| Human Prostate Cancer (LCVMS Cancer Frequency Sets 4 [all tracking generator absorption analysis])* | 157.8 MHz, 1.1495 gigahertz (GHz), 1.153 GHz, 1.356 GHz, 1.393 GHz, 1.4108-1.4760 GHz, 1.579 GHz, 1.612-1.617 GHz, 1.660 GHz, 1.889 GHz, 1.975 GHz, 2.455 GHz; sine and square waveforms | Destructive effects include cessation of mitosis, apoptosis, necrosis, increased cell membrane permeability, protein misfolding, and granulation of cellular mechanics. |
| Human Prostate Cancer (Pulsed signals that showed significant electrical behavior changes) | 278.44 kHz; 6.440 kHz (initiated regular spiking that stayed after signal was shut off); 840 kHz (initiated regular spiking that stayed after signal was shut off); 1.328 MHz; 1.330 MHz; 1.365 MHz; 1.348 MHz; All the above with waveform width of 107 milliseconds and duty cycle of 16% (duty cycle of generator) | Destructive effects include cessation of mitosis, apoptosis, necrosis, increased cell membrane permeability, protein misfolding, and granulation of cellular mechanics. |
| Human Prostate Cancer | 1960 Hz square; 1980 Hz square; 2029 Hz square; | Destructive effects include cessation of mitosis, apoptosis, necrosis, |

-continued

| Cell Type | Bioactive Frequencies Characteristics | Effect(s) on Cell Type |
|---|---|---|
| | 2036 Hz ramp; 2040 Hz ramp; 2417 Hz square; 2020 Hz ramp; 2060 Hz ramp; 2127 Hz ramp; 2634 Hz ramp; 3826 Hz ramp; 7426 Hz; 1170 Hz sine/ramp; 1400 Hz ramp; 1680 Hz ramp; 6982 Hz pulse at 30.2 milliseconds and 21% duty cycle (duty cycle of generator); 11612 Hz square waveform | increased cell membrane permeability, protein misfolding, and granulation of cellular mechanics. |
| Human Prostate Cancer (Boris Pasche breast, prostate, and pancreatic Common Frequencies) | 1,873.477 Hz, 2,221.323 Hz, 6,350.333 Hz, and 10,456.383 Hz; duration of 15 minutes | No significant effects observed after exposure. (Frequencies alleged to have effects on breast, prostate and pancreatic cancers by Boris Pasche.) |
| Human Prostate Cancer (Yoram Palti Novocure Frequencies) | 150 MHz and 200 MHz | No significant effects observed after exposure. (Frequencies alleged to have effects on cancer by Yoram Palti Novocure.) |
| Human Lymphoma Cancer | 971 Hz (square or sine), 9309 Hz (square or sine), 10609 Hz (square or sine) for one hour per day over three consecutive days up to fifteen days; using 2.4 MHz or 3.5 MHz carrier wave; in-vivo | Total/complete human lymphoma cancer cell destruction within 24 hours of exposure, and cessation of mitosis in 12 hours after exposure. |

*Note, in the above Table 1, these descriptors are for internal cross-reference and "LCVMS" refers to "Live Cell Viability Modification System."

The above noted human prostate cancer cells in Table 1 may be cancer cells at least substantially similar to Prostate Cancer Cell lines PC3 (ATCC CRL 1435) with respect to genotype and/or phenotype.

The regular spiking noted in the above Table 1 may refer to a wavenumber shift upon treatment/exposure of the noted electromagnetic energy and/or waveform, similar to the shifts shown in FIG. 8. The Table 1 regular spiking may be as much as minus volts negative spiking in amplitude.

For example, and without limiting the scope of the present invention, treating to increase a desirable cell type, using treatment tool 1000 to output predetermined bioactive electromagnetic frequencies and associated/or characteristics (e.g., waveform 157) transmitted to region being treated 1099, that contains the desirable cell type (and that may contain other different cell types), may fall into two main methodologies: (a) exposing/dosing region being treated 1099 for inducing cellular growth in the treated desirable cell; (b) exposing/dosing region being treated 1099 for inducing cellular division (e.g., mitosis and/or meiosis) in the treated desirable cell; portions thereof; combinations thereof; and/or the like; and any of the above noted desirable cell treatments may be done in vivo, non-invasively, and/or without harming other different cells/tissue types of region being treated 1099.

In some embodiments, increasing a given desirable cell's size, growth rate, and/or division rate, may be done for: healing purposes, such as, but not limited to, healing from some form of trauma (e.g., injury, surgery, burn, and/or the like); to repair and/or improve a particular body system (such as, but not limited to the circulatory system); to repair and/or improve a particular tissue; to strengthen and/or improve immunity and/or the immune system; for cosmetic reasons; for combinations thereof; and/or the like.

In some embodiments, the desirable cell may be selected from: a predetermined type of cell; a predetermined type of tissue; a skin cell; a muscle cell; a connective tissue cell; an eye cell; a gland cell; an endocrine cell; a nerve cell; a breast tissue cell; a penis tissue cell; portions thereof; combinations thereof; and/or the like.

In some embodiments, a given desirable cell may be made more resistant to chemotherapy by making its cell membrane less permeable to chemotherapy drug(s) by exposing/dosing the given desirable cell with predetermined bioactive electromagnetic frequencies and associated/or characteristics (e.g., waveform 157) associated with reduce cell membrane permeability for that given type of desirable cell.

In some embodiments, electro medical tool 100 and/or sensor tool 900 and in conjunction with treatment tool 1000 may be used for a personalized treatment of a particular/given patient. In some embodiments, with respect to personalized treatment, at least one bioactive frequency and/or waveform may be determined (e.g., from electro medical tool 100 and/or sensor tool 900) that may be specific/associated with the given patient and/or with a biopsy, a cell sample in culture, and/or with at least one target cell of that given patient. That determined at least one bioactive frequency and/or waveform may then be applied to region of treatment 1099 of that particular patient. And in that sense the treatment may be personalized (e.g., with using sensor tool 900 [or portion thereof] in conjunction with treatment tool 1000.

In some embodiments, at least one biopsy of target cell(s) may be taken from a given patient; then at least a portion of that biopsy may be exposed to and tested with electro medical tool 100 (and while that at least a portion of that biopsy may be alive) to determine a bioactive frequency and/or waveform of that tested biopsy that may result in a particular cellular outcome/behavior; and then that determined bioactive frequency and/or waveform may be applied to region of treatment 1099 using treatment tool 1000, wherein the biopsy may have been taken from region of treatment 1099—that is, the determined bioactive frequency and/or waveform determined may be personalized with respect to that particular patient and/or that patient's biopsy. In some embodiments, the biopsy may be of an undesirable cell or of a desirable cell.

In some embodiments, sensor tool 900 (and in conjunction with the coils 1001*a* and 1001*b*, in some embodiments) may be used to expose and test at least one target cell of a given patient, and while that at least one target cell may still be alive and part of the given patient, to determine a bioactive frequency and/or waveform of that at least one target cell that may result in a particular cellular outcome/ behavior; and then that determined bioactive frequency and/or waveform may be applied to region of treatment 1099 using treatment tool 1000, wherein the at least one target cell may be within region of treatment 1099—that is, the determined bioactive frequency and/or waveform determined may be personalized with respect to that particular patient and/or that patient's at least one target cell. In embodiments, the at least one target cell may be of an undesirable cell or of a desirable cell.

Figure 11:
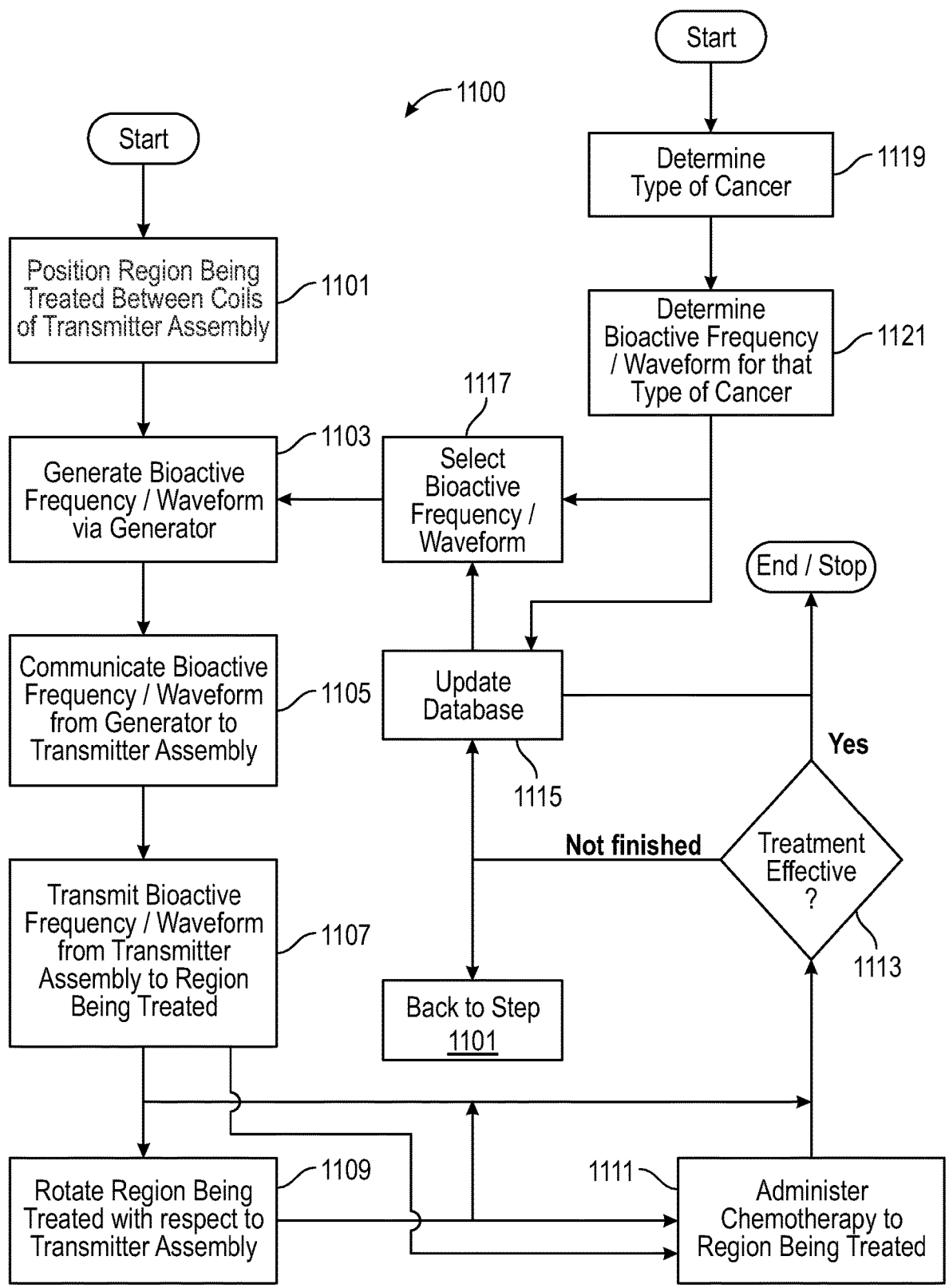
FIG. 11 may depict a flow diagram of at least some steps in a cancer treatment method.

FIG. 11 may depict a flow diagram of at least some steps in a cancer treatment method 1100. In some embodiments, method 1100 may be a treatment method configured to selectively harm a type of cancer in at least one type of organism, such as, but not limited to, a human, a mammal, a vertebrate, or the like. In some embodiments, method 1100 may comprise steps: 1101, 1103, 1105, and 1107. In some embodiments, step 1101 may occur before step 1107. In some embodiments, method 1100 may comprise at least one additional step selected from steps: 1109, 1111, 1113, 1115, and/or 1117. In some embodiments, method 1100 may comprise at least one additional step selected from steps: 1119 and/or 1121. In some embodiments, method 1100 may comprise at least one additional step selected from steps: 1109, 1111, 1113, 1115, 1117, 1119, and/or 1121.

Continuing discussing FIG. 11, in some embodiments, step 1101 may be a step of positioning region being treated 1099 between coils (e.g., coil 1101*a* and coil 1101*b*) of transmitter assembly 1001. In some embodiments, region being treated 1099 may be the organism/patient or portion thereof. In some embodiments, the coils of transmitter assembly 1001 may be opposing (or transmitter assembly 1001 may comprise opposing coils). In some embodiments, the opposing coils of transmitter assembly 1001 may be concentrically spaced apart from each other by a minimum distance, wherein that minimum distance may be sized to fit the region being treated 1099 between those opposing coils of transmitter assembly 1001. In some embodiments, the coils may be positioned substantially (mostly) concentrically to each other, with region being treated 1099 disposed between the coils. In some embodiments, one or both coils may physically touch region being treated 1099. In some embodiments, one or both coils may not physically touch region being treated 1099. In some embodiments, one or both coils may be attached to an exterior of region being treated 1099. In some embodiments, one or both coils may be attached to an exterior of region being treated 1099 using strapping, straps, Velcro, buckles, snaps, ties, and/or other similar removable mechanical fasteners. In some embodiments, step 1101 may progress to step 1103.

Continuing discussing FIG. 11, in some embodiments, step 1103 may be a step of generating the bioactive frequency and/or waveform from a generator, such as, but not limited to frequency Generator/waveform Generator 1011. Note, this generated bioactive frequency and/or waveform from step 1103 may have already been previously determined to be bioactive with respect to the particular type of cancer being treated, see e.g., step 1121, electro medical tool 100 and/or sensor tool 900. Note, this generated bioactive frequency and/or waveform from step 1103 may have already been previously determined to be substantially (mostly) nonharmful to non-cancerous cells of being treated 1099. In some embodiments, step 1103 may progress to step 1105.

Continuing discussing FIG. 11, in some embodiments, step 1105 may be a step of communicating the step 1103 generated bioactive frequency/waveform from the generator (e.g., generator 1011) to the transmitter assembly 1001. In some embodiments, this communication may utilize at least one circuit of the treatment tool 1000. In some embodiments, the at least one circuit may comprise at least one broadband power amplifier (e.g., amplifier 1009) that may be operatively linked to both the generator (e.g., generator 1011) and to the transmitter assembly 1001. In some embodiments, the at least one circuit may comprise the impedance matching network that may be operatively linked to the broadband power amplifier (e.g., amplifier 1009) and to the transmitter assembly 1001. In some embodiments, the at least one circuit may comprise the at least one broadband power amplifier (e.g., amplifier 1009) and the impedance matching network. In some embodiments, this communication may utilize the impedance matching network. In some embodiments, this communication may pass through amplifier 1009, then to attenuator 1007, then to antenna tuner 1005, and then to transmitter assembly 1001. See e.g., FIG. 10. In some embodiments, step 1105 may progress to step 1107.

Continuing discussing FIG. 11, in some embodiments, step 1107 may be a step of transmitting the generated and communicated bioactive frequency/waveform to region being treated 1099 from transmitter assembly 1001. In some embodiments, step 1107 may be a step of transmitting the generated and communicated bioactive frequency/waveform to region being treated 1099 from coil 1001*a* and/or from coil 1001*b*. In some embodiments, step 1107 may be executed and/or carried out in an in vivo and non-invasive treatment setting with respect to the given organism being treated (e.g., a human, a mammal, or a vertebrate animal). In some embodiments, step 1107 may be executed and/or carried out in non-contact treatment manner with respect to the given organism being treated. In some embodiments, this transmission of step 1107 may continue for a predetermined amount of time (duration). In some embodiments, step 1107 may progress to step 1109, step 1111, or step 1113. In some embodiments, step 1107 may progress to step 1109 when rotation during transmission of the bioactive frequency/ waveform may be desired. In some embodiments, step 1107 may progress to step 1111 when administering at least one chemotherapy drug during and/or after transmission of the bioactive frequency/waveform may be desired. In some embodiments, step 1107 may progress to step 1113 when neither step 1109 nor step 1111 are being carried out.

Continuing discussing FIG. 11, in some embodiments, step 1109 may be a step of rotating region being treated 1099 with respect to the coils of transmitter assembly 1001. In some embodiments, the coils of transmitter assembly 1001 may be fixed and region being treated 1099 may be rotated with respect to the coils of transmitter assembly 1001. In some embodiments, region being treated 1099 may be fixed and the coils of transmitter assembly 1001 may be rotated around respect to region being treated 1099. In some embodiments, both region being treated 1099 and the coils of transmitter assembly 1001 may rotate with respect to each other. In some embodiments, step 1109 may occur concurrently with step 1107. In some embodiments, step 1109 may be omitted from method 1100. In some embodiments, step 1109 may progress to step 1111 or to step 1113. In some embodiments, step 1109 may progress to step 1111 when administering at least one chemotherapy drug during and/or after transmission of the bioactive frequency/waveform may be desired; and/or when administering at least one chemotherapy drug during and/or after transmission of the step 1109 rotation. In some embodiments, step 1109 may progress to step 1113 when step 1111 is not being carried out.

Continuing discussing FIG. 11, in some embodiments, step 1111 may be a step of administering at least one chemotherapy drug to the organism (e.g., a human, a mammal, or a vertebrate) being treated in method 1100. In some embodiments, the means for administering the at least one chemotherapy drug to the given organism, may be a means readily used by an oncologist, such as, but not limited to, injection (intravenous [IV], intramuscular [IM], subcutaneous [SC], intrathecally), IV, orally, sublingual, buccal, rectally, vaginal, ocular, otic, nasal, inhalation, topical, cutaneous, transdermal, implant, combinations thereof, and/or the like. In some embodiments, the specific bioactive frequency/waveform transmitted in step 1107 (and/or in step 1109) may result in increased cell membrane permeability of the cancer cells within region being treated 1099; which in turn may make these cancer cells more likely uptake and/or be affected by chemotherapy drug(s). In some embodiments, during and after step 1107 the plurality of cancer cells (within/part of region being treated 1099) has increased cell membrane permeability as a result of step 1107, rendering the plurality of cancer cells more susceptible to uptake of the at least one chemotherapy drug as compared to the plurality of cancer cells before step 1107, wherein during or after step 1107 the method may comprise step 1111 of administering the at least one chemotherapy drug to the given organism/patient. In some embodiments, step 1111 may occur after or during steps 1107 and/or 1109. In some embodiments, step 1111 may be omitted from method 1100. In some embodiments, step 1111 may progress to step 1113.

Continuing discussing FIG. 11, in some embodiments, step 1113 may be a step of determining if the method 1100 treatment was sufficiently effective. In some embodiments, step 1113 may comprise using one or more diagnostic tests used to monitor status of a given cancer; and may include various blood work, labs, assays, biopsies, scans, combinations thereof, and/or the like. In some embodiments, if step 1113 determines treatment method 1100 to be sufficiently effective, then step 1113 may progress to step 1115 for updating a database (e.g., database 1037 and/or 137) with results of the treatment method 1100, including the step 1113 diagnostic tests results and/or the bioactive frequency/waveform used in the treatment and the type of cancer treated. In some embodiments, if step 1113 determines treatment method 1100 to be sufficiently effective, then step 1113 may cause method 1100 to stop/end. In some embodiments, if step 1113 determines treatment method 1100 to not be finished, then step 1113 may progress to step 1115 for updating a database (e.g., database 1037 and/or 137) with results of the treatment method 1100, including the step 1113 diagnostic tests results and/or the bioactive frequency/waveform used in the treatment and the type of cancer treated. In some embodiments, if step 1113 determines treatment method 1100 to not be finished, then step 1113 may progress back to step 1101 for another round of treatment. Note, such subsequent rounds of treatment may occur on different days. In some embodiments, step 1113 may be omitted from method 1100.

Continuing discussing FIG. 11, in some embodiments, step 1115 may be a step of updating a database (e.g., database 1037 and/or 137). In some embodiments, step 1115 may be a documenting step. In some embodiments, the database (e.g., database 1037 and/or 137) may non-transitorily store a plurality of bioactive energy of predetermined characteristics (i.e., a plurality of bioactive frequencies and/or waveforms for a given type of cancer). In some embodiments, step 1115 may be reached from step 1113 and/or from step 1121. In some embodiments, when step 1115 may be reached from step 1113, then the database (e.g., database 1037 and/or 137) may be updated with the results of the step 1113 diagnostic tests and/or the bioactive frequency/waveform used in the treatment and the type of cancer treated. In some embodiments, when step 1115 may be reached from step 1121, then the database (e.g., database 1037 and/or 137) may be updated with the frequencies and/or the waveforms that have been determined to effective in treating the particular type of cancer the results; wherein these frequencies and/or waveforms are now termed bioactive with respect to that particular type of cancer. In some embodiments, in step 1115 the database (e.g., database 1037 and/or 137) may also be updated with the determined bioactive frequencies and/or the waveforms are at least substantially non-harmful to other types of cells that are different types of cells from the particular type of cancer. See Table 1, which may show a subset of bioactive frequencies and/or waveforms with respect to human prostate cancer and lymphoma cancer. The information of Table 1 may be included in the database (e.g., database 1037 and/or 137). In some embodiments, step 1115 may be omitted from method 1100. In some embodiments, step 1115 may progress to step 1117.

Continuing discussing FIG. 11, in some embodiments, step 1117 may be a step of selecting at least one bioactive frequency/waveform for a given particular type of cancer to be used in a given treatment session using method 1100. In some embodiments, this selection may be from the database (e.g., database 1037 and/or 137) that non-transitorily stores lists and/or menus of the bioactive frequencies and/or waveforms for a particular type of cancer. In some embodiments, step 1117 may be omitted from method 1100. In some embodiments, step 1117 may progress to step 1103.

Continuing discussing FIG. 11, in some embodiments, step 1119 may be a step of determining the particular type of cancer(s) that the given organism to be treated may have. In some embodiments, step 1119 may utilize any present day and/or established diagnostic test and/or tool for determining the particular cancer(s) of the given organism. If the particular type of cancer to be treated is already known, then step 1119 may not be necessary. In some embodiments, step 1119 may be omitted from method 1100. In some embodiments, step 1119 may progress to step 1121.

Continuing discussing FIG. 11, in some embodiments, step 1121 may be a step of determining/testing what frequencies and/or waveforms may be bioactive (e.g., harmful) to the given identified particular type of cancer. In some embodiments, step 1121 may utilize electro medical tool 100 and/or sensor tool 900 to determine such bioactive frequencies and/or waveforms. See e.g., FIG. 1 through FIG. 9; and their above discussions. In some embodiments, the step of determining/testing at least some cancer cells, from the given patient/organism, for bioactive frequencies/waveforms (i.e., step 1121), may occur in an in vivo and mildly invasive manner (e.g., when sensor tool 900 may be used). In some embodiments, step 1121 may involve controlled and systemic sweeping through at least portions of the electromagnetic spectrum and/or the acoustic spectrum to determine such bioactive frequencies and/or waveforms. See also, Table 1, which may show a subset of such determined bioactive frequencies and/or waveforms. If the particular type of cancer to be treated is already known and its bioactive frequencies and/waveforms are already known, then step 1121 may not be necessary. In some embodiments, step 1121 may be omitted from method 1100. In some embodiments, step 1121 may progress to step 1115 and/or to step 1117.

In some embodiments, using sensor tool 900 to carry out step 1121 may comprise sub-steps of: (i) placing electrodes (e.g., electrodes 909) into the at least some cancer cells (e.g., region of tissue 999); (ii) using the generator 1011 and the transmitter assembly 1001 to sweep and transmit through a range of electromagnetic frequencies and/or a range of acoustic frequencies; and (iii) using the placed electrodes as sensors to sense changes in the at least some cancer cells that correlate harm to the at least some cancer cells to a particular electromagnetic frequency selected from the range of electromagnetic frequencies and/or to a particular acoustic frequency selected from the range of acoustic frequencies, generated and transmitted in the sub-step (ii). In some embodiments, the particular electromagnetic frequency and/or the particular acoustic frequency that correlate with the harm to the at least some cancer cells are deemed the determined at least one electromagnetic characteristic and/or are deemed the determined at least one acoustic characteristic, which are the bioactive frequencies and/or waveforms for that particular type of cancer for that particular patient/organism. In some embodiments, step 1115 may be a step of documenting the determined at least one electromagnetic characteristic and/or are deemed the determined at least one acoustic characteristic that correlate with the harm to the at least some cancer cells by updating the database (e.g., database 1037 and/or 137).

In some embodiments, step 1119 and/or step 1121 may be used in a personal medicine treatment plan, wherein determination of the applicable bioactive frequencies/waveforms that are harmful to the particular type of cancer are tested on cancer cells from that particular patient to be treated and not on that type cancer cells from a cell line or from another organism.

In some embodiments, treatment method 1100 may comprise a step of controlling at least some of the steps of method 1100 (e.g., steps 1103, 1105, and/or 1107) from a computer (e.g., computer 1033) that may be operatively linked with generator 1011 and/or with the circuit (e.g., amplifier 1009, attenuator 1007, and/or antenna tuner 1005).

Note, "region being treated 1099" may be used interchangeably with "region to be treated" and/or with "region already/previously treated."

The electromagnetic characteristics that may be generated, varied, controlled, and applied from electro medical tool 100, sensor tool 900, treatment tool 1000 to a given set of living cell(s)/tissue 199, region of tissue 999, and/or region being treated 1099 may comprise: frequency (or wavelength) (selected from the entire electromagnetic spectrum and/or from the acoustic spectrum); waveform (e.g., DC, sine, square, sawtooth, rising, falling, inversions, amplitude variance, gain, duty cycle variance, and/or the like); harmonic(s) of a given waveform; energy level applied; duration of exposure (e.g., in milliseconds [or other unit of time]); portions thereof; combinations thereof; and/or the like. In some embodiments, the bioactive frequencies and/or waveforms may be applied by use of one or more carrier waves.

The electromagnetic characteristics that may be generated, varied, controlled, and applied from various generators disclosed herein (e.g., 101, 919, and/or 1011) to a given set of living cell(s)/tissue 199, region of tissue 999, and/or region being treated 1099 may comprise: frequency (or wavelength) (selected from the entire electromagnetic spectrum and/or from the acoustic spectrum); waveform (e.g., DC, sine, square, sawtooth, rising, falling, inversions, amplitude variance, gain, duty cycle variance, and/or the like); harmonic(s) of a given waveform; energy level applied; duration of exposure (e.g., in milliseconds [or other unit of time]); portions thereof; combinations thereof; and/or the like. In some embodiments, the bioactive frequencies and/or waveforms may be applied by use of one or more carrier waves.

Note, any coil noted herein (such as, but not limited to, coil 1001*a* and/or coil 1001*b*) may have various predetermined characteristics, such as, but not limited to, quantity of turns, conductive material of construction (e.g., copper), insulating material of construction, conductive material dimensions (e.g., gauge, diameter, and/or length), insulating material dimension (e.g., wall thickness), portions thereof, combinations thereof, and/or the like.

In some embodiments, treatment tool 1000 may be used for treating at least one cell type of a patient. In some embodiments, treatment tool 1000 may be used in at least one method for treating at least one cell type of a patient. In some embodiments, treatment tool 1000 may be used for treating at least one cancer cell type of a patient. In some embodiments, treatment tool 1000 may be used in at least one method for treating at least one cancer cell type of a patient. In some embodiments, treatment tool 1000 may be used for treating at least one infected cell type of a patient. In some embodiments, treatment tool 1000 may be used in at least one method for treating at least one infected cell type of a patient. In some embodiments, treatment tool 1000 may be used in at least one method for chemotherapy (or improved chemotherapy over traditional chemotherapy). In some embodiments, treatment tool 1000 may be used in at least one method for chemotherapy (or improved chemotherapy over traditional chemotherapy) by increasing a particular cell type cell membrane permeability. In some embodiments, treatment tool 1000 may be used in at least one method for using a host's natural immune system to target particular host cells exhibiting a particular pathology and/or marked with a predetermined marker. In some embodiments, treatment tool 1000 may be used in at least one method for personalized treatment.

Devices, tools, apparatus, systems, and methods for determining bioactive frequencies and/or waveform characteristics for a particular cellular outcome/behavior of a particular cell type, have been described; and devices, tools, apparatus, systems, and methods for using the determined bioactive frequencies and/or waveform characteristics for a particular cellular outcome/behavior of a particular cell type; and methods for treating cancer using such bioactive frequencies and/or waveforms have been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A treatment method configured to selectively harm a type of cancer in a subject organism, wherein the method comprises steps of:
    (a) positioning a region to be treated of the subject organism between opposing coils of a transmitter assembly, wherein the region to be treated includes a plurality of cancer cells of the type of cancer;
    (b) generating bioactive energy of a predetermined characteristic from a generator, wherein the bioactive energy of the predetermined characteristic has been previously determined to harm the type of cancer;
    (c) communicating the bioactive energy of the predetermined characteristic generated in the step (b) from the generator to the transmitter assembly via a circuit; and
    (d) transmitting the bioactive energy of the predetermined characteristic from the coils of the transmitter assembly to the region to be treated, wherein the bioactive energy of the predetermined characteristic selectively harms the plurality of cancer cells without harming non-cancerous cells, of the region to be treated, which are simultaneously exposed to the bioactive energy of the predetermined characteristic;
        wherein during the step (d) the opposing coils of the transmitter assembly, that are located around the region to be treated, and the region to be treated are rotated with respect to each other, while maintaining the region to be treated being located between the opposing coils;
        wherein the step (d) is executed in an in vivo and non-invasive treatment setting with respect to the subject organism.

2. The treatment method according to claim 1, wherein the type of cancer is human prostate cancer and the bioactive energy of the predetermined characteristic is at least one of: a 450 hertz square waveform, a 2008 hertz square waveform, a 4000 hertz square waveform, a 6022 hertz square waveform, a 14000 hertz sine waveform, or a 20000 hertz sine waveform.

3. The treatment method according to claim 1, wherein the type of cancer is human prostate cancer and the bioactive energy of the predetermined characteristic is: at least one of: a 489 hertz square waveform, a 583 hertz square waveform, a 971.3 hertz square waveform, a 4000 hertz square waveform, a 7402 hertz square waveform, a 10542 hertz square waveform, or a 11300 hertz square waveform.

4. The treatment method according to claim 1, wherein the type of cancer is human prostate cancer and the bioactive energy of the predetermined characteristic is at least one of: a 317 kilohertz sine waveform, a 544 kilohertz sine waveform, a 947 kilohertz sine waveform, a 1.220 megahertz sine waveform, a 2.467 megahertz sine waveform, a 4.812 megahertz sine waveform, a 5.265 megahertz sine waveform, a 5.9 megahertz sine waveform, a 11.300 megahertz sine waveform, a 11.780 megahertz sine waveform, a 17.045 megahertz sine waveform, or a 28.823 megahertz sine waveform.

5. The treatment method according to claim 1, wherein the type of cancer is human prostate cancer and the bioactive energy of the predetermined characteristic is at least one of: 157.8 megahertz, 1.149 gigahertz, 1.153 gigahertz, 1.356 gigahertz, 1.393 gigahertz, 1.410 gigahertz to 1.476 gigahertz, 1.579 gigahertz, 1.612 gigahertz to 1.617 gigahertz, 1.660 gigahertz, 1.889 gigahertz, 1.975 gigahertz, or 2.455 gigahertz; and wherein the bioactive energy of the predetermined characteristic has a sine waveform or a square waveform.

6. The treatment method according to claim 1, wherein the type of cancer is human prostate cancer and the bioactive energy of the predetermined characteristic comprises a waveform width of 107 milliseconds and a duty cycle of 16%; wherein the bioactive energy of the predetermined characteristic is at least one of: 278.44 kilohertz, 6.440 kilohertz, 840 kilohertz, 1.328 megahertz, 1.330 megahertz, 1.365 megahertz, or 1.348 megahertz.

7. The treatment method according to claim 1, wherein the type of cancer is human prostate cancer and the bioactive energy of the predetermined characteristic is at least one: a 1960 hertz square waveform, a 1980 hertz square waveform, a 2029 hertz square waveform, a 2036 hertz ramp waveform, a 2040 hertz ramp waveform, a 2417 hertz square waveform, a 2020 hertz ramp waveform, a 2060 hertz ramp waveform, a 2127 hertz ramp waveform, a 2634 hertz ramp waveform, a 3826 hertz ramp waveform, a 7426 hertz, a 1170 hertz sine waveform, a 1170 hertz ramp waveform, a 1400 hertz ramp waveform, a 1680 hertz ramp waveform, a 6982 hertz pulse waveform at 30.2 milliseconds and a 21% duty cycle, or a 11612 hertz square waveform.

8. The treatment method according to claim 1, wherein the type of cancer is human lymphoma cancer and the bioactive energy of the predetermined characteristic is at least one of: 971 hertz, 9309 hertz, or 10609 hertz; wherein a duration of transmission of the bioactive energy of the predetermined characteristic to the region being treated is for at least one hour per day over at least fifteen consecutive days in an in vivo setting.

9. The treatment method according to claim 1, wherein the opposing coils of the transmitter assembly are concentrically spaced apart from each other by a minimum distance, wherein the minimum distance is sized to fit the region to be treated between the opposing coils.

10. The treatment method according to claim 1, wherein the opposing coils are fixed and the region to be treated is caused to be rotated between the opposing coils.

11. The treatment method according to claim 1, wherein the region to be treated is fixed and the opposing coils are caused to be rotated around the region to be treated.

12. The treatment method according to claim 1, wherein the circuit comprises at least one broadband power amplifier that is operatively linked to both the generator and to the transmitter assembly.

13. The treatment method according to claim 12, wherein the circuit further comprises an impedance matching network that is operatively linked to the at least one broadband power amplifier and to the transmitter assembly.

14. The treatment method according to claim 1, wherein the treatment method prior to the step (b) further comprises a step of selecting the bioactive energy of the predetermined characteristic to be generated in the step (b) from a database that is non-transitorily storing a plurality of bioactive energy of predetermined characteristics.

15. The treatment method according to claim 14, wherein prior to the step of selecting the bioactive energy of the predetermined characteristic to be generated in the step (b), the method further comprises a step of determining the type of cancer.

16. The treatment method according to claim 15, wherein after the step of determining the type of cancer, the method further comprises a step of testing at least some cancer cells selected from the plurality of cancer cells to determine at least one electromagnetic characteristic and/or to determine at least one acoustic characteristic that harms the at least some cancer cells; wherein the determined at least one electromagnetic characteristic and/or the determined at least one acoustic characteristic are deemed the bioactive energy of the predetermined characteristic.

17. The treatment method according to claim 16, wherein the step of testing the at least some cancer cells occurs in an in vivo and mildly invasive manner.

18. The treatment method according to claim 16, wherein the step of testing the at least some cancer cells comprises sub-steps of: (i) placing electrodes into the at least some cancer cells; (ii) using the generator and the transmitter assembly to sweep and transmit through a range of electromagnetic frequencies and/or a range of acoustic frequencies; and (iii) using the placed electrodes as sensors to sense changes in the at least some cancer cells that correlate harm to the at least some cancer cells to a particular electromagnetic frequency selected from the range of electromagnetic frequencies and/or to a particular acoustic frequency selected from the range of acoustic frequencies, generated and transmitted in the sub-step (ii); wherein the particular electromagnetic frequency and/or the particular acoustic frequency that correlate with the harm to the at least some cancer cells are deemed the determined at least one electromagnetic characteristic and/or are deemed the determined at least one acoustic characteristic.

19. The treatment method according to claim 16, wherein the step of testing the at least some cancer cells comprises a sub-step (iv) documenting the determined at least one electromagnetic characteristic and/or the determined at least one acoustic characteristic that harms the at least some cancer cells.

20. The treatment method according to claim 1, wherein during and after the step (d) the plurality of cancer cells has increased cell membrane permeability as a result of the step (d), rendering the plurality of cancer cells more susceptible to uptake of at least one chemotherapy drug as compared to the plurality of cancer cells before the step (d), wherein during or after the step (d) the method further comprises a step of administering the at least one chemotherapy drug to the subject organism.

21. The treatment method according to claim 1, wherein the treatment method further comprises a step of controlling the steps (b), (c), or (d) from a computer that is operatively linked with the generator and/or with the circuit.

22. The treatment method according to claim 1, wherein the region to be treated is the subject organism or portion thereof.

23. The treatment method according to claim 1, wherein the step (a) occurs before the step (d).

24. A treatment method configured to selectively harm a type of cancer in a subject organism, wherein the method comprises steps of:
(a) positioning a region to be treated of the subject organism between opposing coils of a transmitter assembly, wherein the region to be treated includes a plurality of cancer cells of the type of cancer;
(b) generating bioactive energy of a predetermined characteristic from a generator, wherein the bioactive energy of the predetermined characteristic has been previously determined to harm the type of cancer;
(c) communicating the bioactive energy of the predetermined characteristic generated in the step (b) from the generator to the transmitter assembly via a circuit; and
(d) transmitting the bioactive energy of the predetermined characteristic from the coils of the transmitter assembly to the region to be treated, wherein the bioactive energy of the predetermined characteristic selectively harms the plurality of cancer cells without harming non-cancerous cells, of the region to be treated, which are simultaneously exposed to the bioactive energy of the predetermined characteristic;
wherein the step (d) is executed in an in vivo and non-invasive treatment setting with respect to the subject organism;
wherein the circuit comprises at least one broadband power amplifier that is operatively linked to both the generator and to the transmitter assembly;
wherein the circuit further comprises an impedance matching network that is operatively linked to the at least one broadband power amplifier and to the transmitter assembly.

25. The treatment method according to claim 24, wherein the type of cancer is human prostate cancer and the bioactive energy of the predetermined characteristic is at least one of: a 450 hertz square waveform, a 2008 hertz square waveform, a 4000 hertz square waveform, a 6022 hertz square waveform, a 14000 hertz sine waveform, or a 20000 hertz sine waveform.

26. The treatment method according to claim 24, wherein the type of cancer is human prostate cancer and the bioactive energy of the predetermined characteristic is: at least one of: a 489 hertz square waveform, a 583 hertz square waveform, a 971.3 hertz square waveform, a 4000 hertz square waveform, a 7402 hertz square waveform, a 10542 hertz square waveform, or a 11300 hertz square waveform.

27. The treatment method according to claim 24, wherein the type of cancer is human prostate cancer and the bioactive energy of the predetermined characteristic is at least one of: a 317 kilohertz sine waveform, a 544 kilohertz sine waveform, a 947 kilohertz sine waveform, a 1.220 megahertz sine waveform, a 2.467 megahertz sine waveform, a 4.812 megahertz sine waveform, a 5.265 megahertz sine waveform, a 5.9 megahertz sine waveform, a 11.300 megahertz sine waveform, a 11.780 megahertz sine waveform, a 17.045 megahertz sine waveform, or a 28.823 megahertz sine waveform.

28. The treatment method according to claim 24, wherein the type of cancer is human prostate cancer and the bioactive energy of the predetermined characteristic is at least one of: 157.8 megahertz, 1.149 gigahertz, 1.153 gigahertz, 1.356 gigahertz, 1.393 gigahertz, 1.410 gigahertz to 1.476 gigahertz, 1.579 gigahertz, 1.612 gigahertz to 1.617 gigahertz, 1.660 gigahertz, 1.889 gigahertz, 1.975 gigahertz, or 2.455 gigahertz; and wherein the bioactive energy of the predetermined characteristic has a sine waveform or a square waveform.

29. The treatment method according to claim 24, wherein the type of cancer is human prostate cancer and the bioactive energy of the predetermined characteristic comprises a waveform width of 107 milliseconds and a duty cycle of 16%; wherein the bioactive energy of the predetermined characteristic is at least one of: 278.44 kilohertz, 6.440 kilohertz, 840 kilohertz, 1.328 megahertz, 1.330 megahertz, 1.365 megahertz, or 1.348 megahertz.

30. The treatment method according to claim 24, wherein the type of cancer is human prostate cancer and the bioactive energy of the predetermined characteristic is at least one: a 1960 hertz square waveform, a 1980 hertz square waveform, a 2029 hertz square waveform, a 2036 hertz ramp waveform, a 2040 hertz ramp waveform, a 2417 hertz square waveform, a 2020 hertz ramp waveform, a 2060 hertz ramp waveform, a 2127 hertz ramp waveform, a 2634 hertz ramp waveform, a 3826 hertz ramp waveform, a 7426 hertz, a 1170 hertz sine waveform, a 1170 hertz ramp waveform, a 1400 hertz ramp waveform, a 1680 hertz ramp waveform, a 6982 hertz pulse waveform at 30.2 milliseconds and a 21% duty cycle, or a 11612 hertz square waveform.

31. The treatment method according to claim 24, wherein the type of cancer is human lymphoma cancer and the bioactive energy of the predetermined characteristic is at least one of: 971 hertz, 9309 hertz, or 10609 hertz; wherein a duration of transmission of the bioactive energy of the predetermined characteristic to the region being treated is for at least one hour per day over at least fifteen consecutive days in an in vivo setting.

32. The treatment method according to claim 24, wherein the opposing coils of the transmitter assembly are concentrically spaced apart from each other by a minimum distance, wherein the minimum distance is sized to fit the region to be treated between the opposing coils.

33. The treatment method according to claim 24, wherein during the step (d) the opposing coils of the transmitter assembly, that are located around the region to be treated, and the region to be treated are rotated with respect to each other, while maintaining the region to be treated being located between the opposing coils; wherein the opposing coils are fixed and the region to be treated is caused to be rotated between the opposing coils.

34. The treatment method according to claim 24, wherein during the step (d) the opposing coils of the transmitter assembly, that are located around the region to be treated, and the region to be treated are rotated with respect to each other, while maintaining the region to be treated being located between the opposing coils; wherein the region to be treated is fixed and the opposing coils are caused to be rotated around the region to be treated.

35. The treatment method according to claim 24, wherein the treatment method prior to the step (b) further comprises a step of selecting the bioactive energy of the predetermined characteristic to be generated in the step (b) from a database that is non-transitorily storing a plurality of bioactive energy of predetermined characteristics.

36. The treatment method according to claim 35, wherein prior to the step of selecting the bioactive energy of the predetermined characteristic to be generated in the step (b), the method further comprises a step of determining the type of cancer.

37. The treatment method according to claim 36, wherein after the step of determining the type of cancer, the method further comprises a step of testing at least some cancer cells selected from the plurality of cancer cells to determine at least one electromagnetic characteristic and/or to determine at least one acoustic characteristic that harms the at least some cancer cells; wherein the determined at least one electromagnetic characteristic and/or the determined at least one acoustic characteristic are deemed the bioactive energy of the predetermined characteristic.

38. The treatment method according to claim 37, wherein the step of testing the at least some cancer cells occurs in an in vivo and mildly invasive manner.

39. The treatment method according to claim 37, wherein the step of testing the at least some cancer cells comprises sub-steps of: (i) placing electrodes into the at least some cancer cells; (ii) using the generator and the transmitter assembly to sweep and transmit through a range of electromagnetic frequencies and/or a range of acoustic frequencies; and (iii) using the placed electrodes as sensors to sense changes in the at least some cancer cells that correlate harm to the at least some cancer cells to a particular electromagnetic frequency selected from the range of electromagnetic frequencies and/or to a particular acoustic frequency selected from the range of acoustic frequencies, generated and transmitted in the sub-step (ii); wherein the particular electromagnetic frequency and/or the particular acoustic frequency that correlate with the harm to the at least some cancer cells are deemed the determined at least one electromagnetic characteristic and/or are deemed the determined at least one acoustic characteristic.

40. The treatment method according to claim 37, wherein the step of testing the at least some cancer cells comprises a sub-step (iv) documenting the determined at least one electromagnetic characteristic and/or the determined at least one acoustic characteristic that harms the at least some cancer cells.

41. The treatment method according to claim 24, wherein during and after the step (d) the plurality of cancer cells has increased cell membrane permeability as a result of the step (d), rendering the plurality of cancer cells more susceptible to uptake of at least one chemotherapy drug as compared to the plurality of cancer cells before the step (d), wherein during or after the step (d) the method further comprises a step of administering the at least one chemotherapy drug to the subject organism.

42. The treatment method according to claim 24, wherein the treatment method further comprises a step of controlling the steps (b), (c), or (d) from a computer that is operatively linked with the generator and/or with the circuit.

43. The treatment method according to claim 24, wherein the region to be treated is the subject organism or portion thereof.

44. The treatment method according to claim 24, wherein the step (a) occurs before the step (d).

* * * * *